United States Patent [19]
Kuo-Petravic et al.

[11] Patent Number: 5,375,156
[45] Date of Patent: Dec. 20, 1994

[54] METHOD AND APPARATUS FOR 3-D COMPUTER TOMOGRAPHY

[75] Inventors: Gioietta Kuo-Petravic, Lawrenceville; Rolf Hupke, Little Silver, both of N.J.

[73] Assignee: Siemens Medical Systems, Inc., Iselin, N.J.

[21] Appl. No.: 860,854

[22] Filed: Mar. 31, 1992

[51] Int. Cl.$^5$ .......................................... G01N 23/083
[52] U.S. Cl. ....................... 378/9; 378/15; 378/901; 364/413.15; 364/413.19; 364/413.21
[58] Field of Search .................. 378/4, 9, 15, 17, 901; 364/413.15, 413.19, 413.2, 413.21

[56] References Cited

U.S. PATENT DOCUMENTS

| | | | |
|---|---|---|---|
| 4,875,165 | 10/1989 | Fencil et al. | 364/413.22 |
| 5,038,371 | 8/1991 | Janssen et al. | 378/197 |
| 5,040,203 | 8/1991 | Janssen et al. | 378/197 |
| 5,068,882 | 11/1991 | Eberhard | 378/4 |
| 5,170,439 | 12/1992 | Zeng et al. | 382/6 |

OTHER PUBLICATIONS

"Practical cone-beam algorithm", Feldkamp et al., J. Opt. Soc. Am. A, vol. 1, No. 6, (Jun. 1984), pp. 612–619.

"Feasible cone beam scanning methods for exact reconstruction in three-dimensional tomography", Kudo et al., J. Opt. Soc. Am. A, vol. 7, No. 12. (Dec. 1990), pp. 2169–2183.

"Cone-beam tomography: recent advances and a tutorial review", Smith, Optical Engineering, vol. 29, No. 5, (May 1990), pp. 524–534.

"An Inversion formula for cone-beam reconstruction", Tuy, Siam J. Appl. Math., vol. 43, No. 3 (Jun. 1983), pp. 546–552.

"Principles of Computerized Tomographic Imaging" Kak et al., IEEE Press, IEEE Order No. PC02071, 1988, pp. 104–112.

*Primary Examiner*—Paul M. Dzierzynski
*Assistant Examiner*—David V. Bruce
*Attorney, Agent, or Firm*—Lawrence C. Edelman

[57] ABSTRACT

A computer tomographic system provides 3-D (three-dimensional) images of interior portions of a body, by scanning in a plurality of substantially orthogonal planes to obtain projection data on a 2-D (two-dimensional) detector surface, for each rotational position within a scanning plane and for each scanning plane. Reconstruction of the image data is obtained by back-projecting the projection data from each plane, and adding together the backprojected values from each plane for providing a 3-D mesh of the image data.

16 Claims, 26 Drawing Sheets

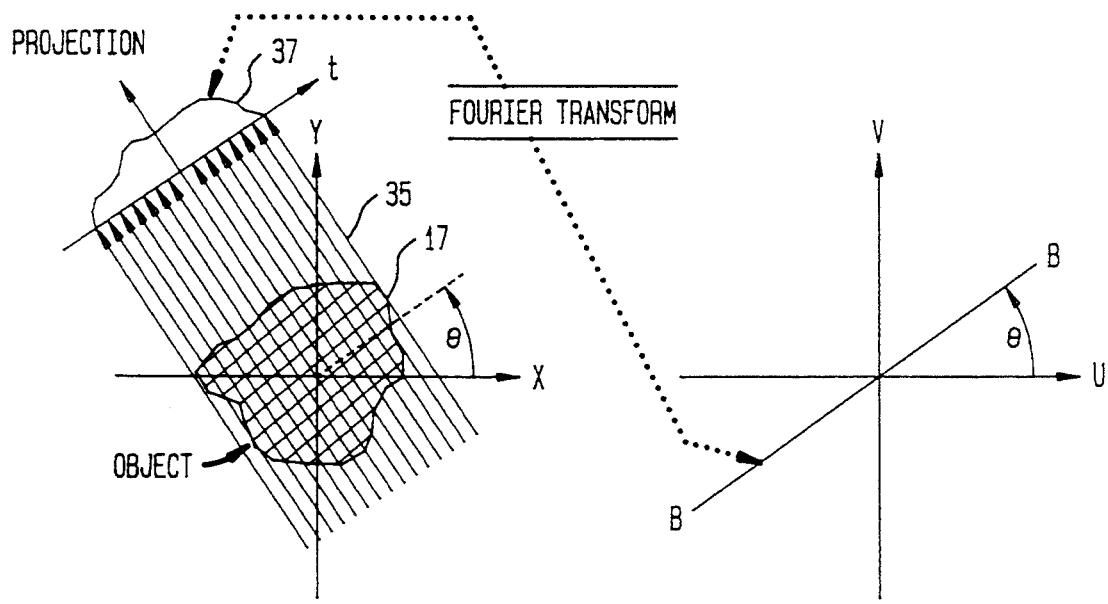
FIG. 11A
SPACE DOMAIN
FIG. 11B
FREQUENCY DOMAIN
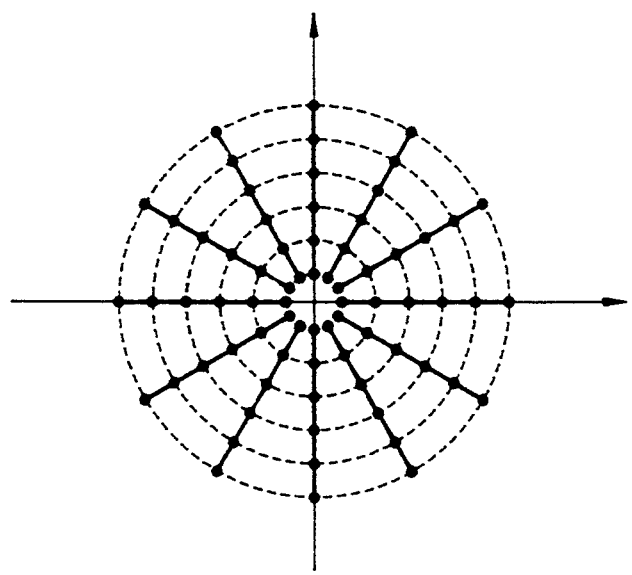
FIG. 11C
FREQUENCY DOMAIN

CS - CORONAL SLICE
SS - SAGITTAL SLICE
TS - TRANSAXIAL SLICE

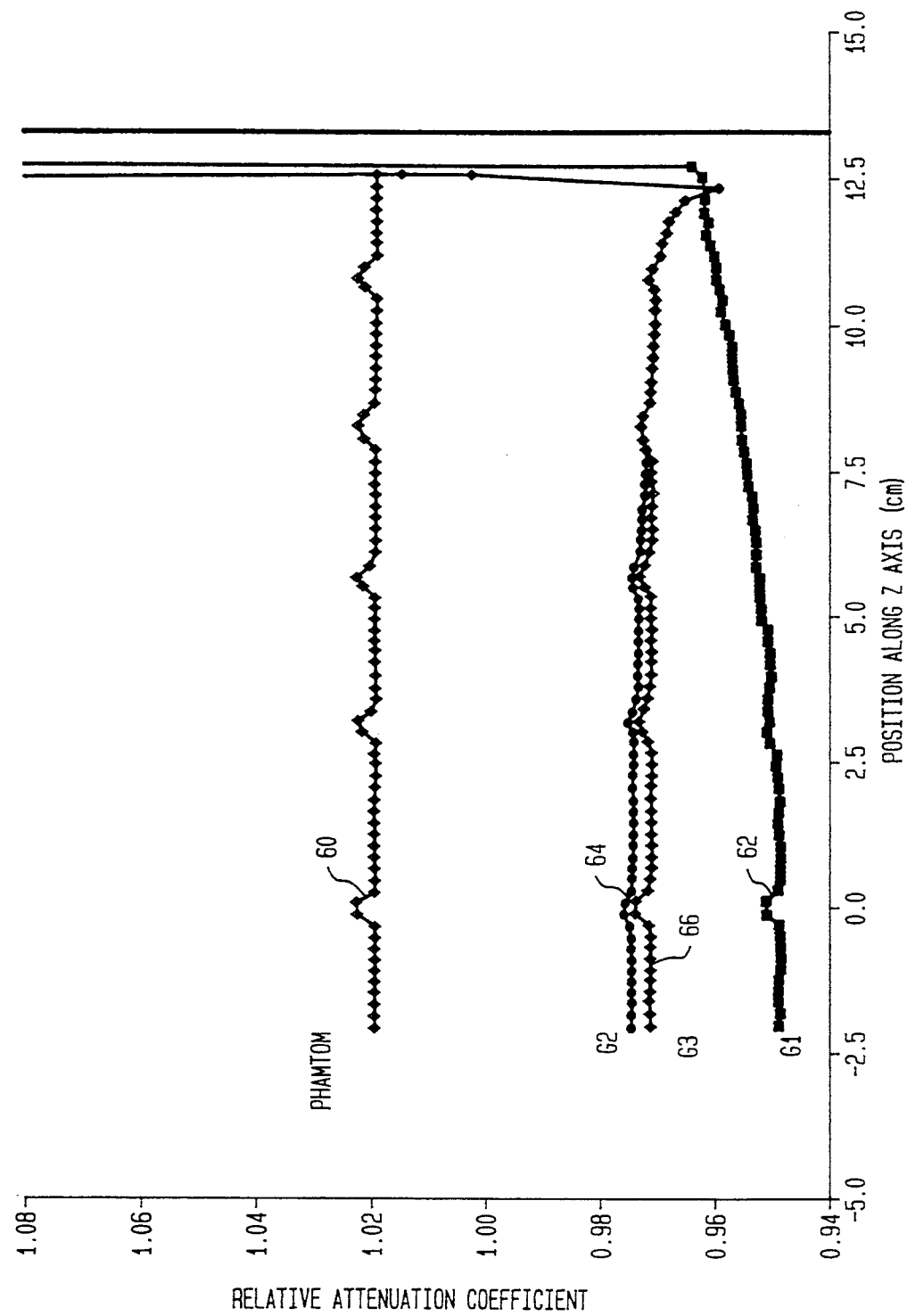

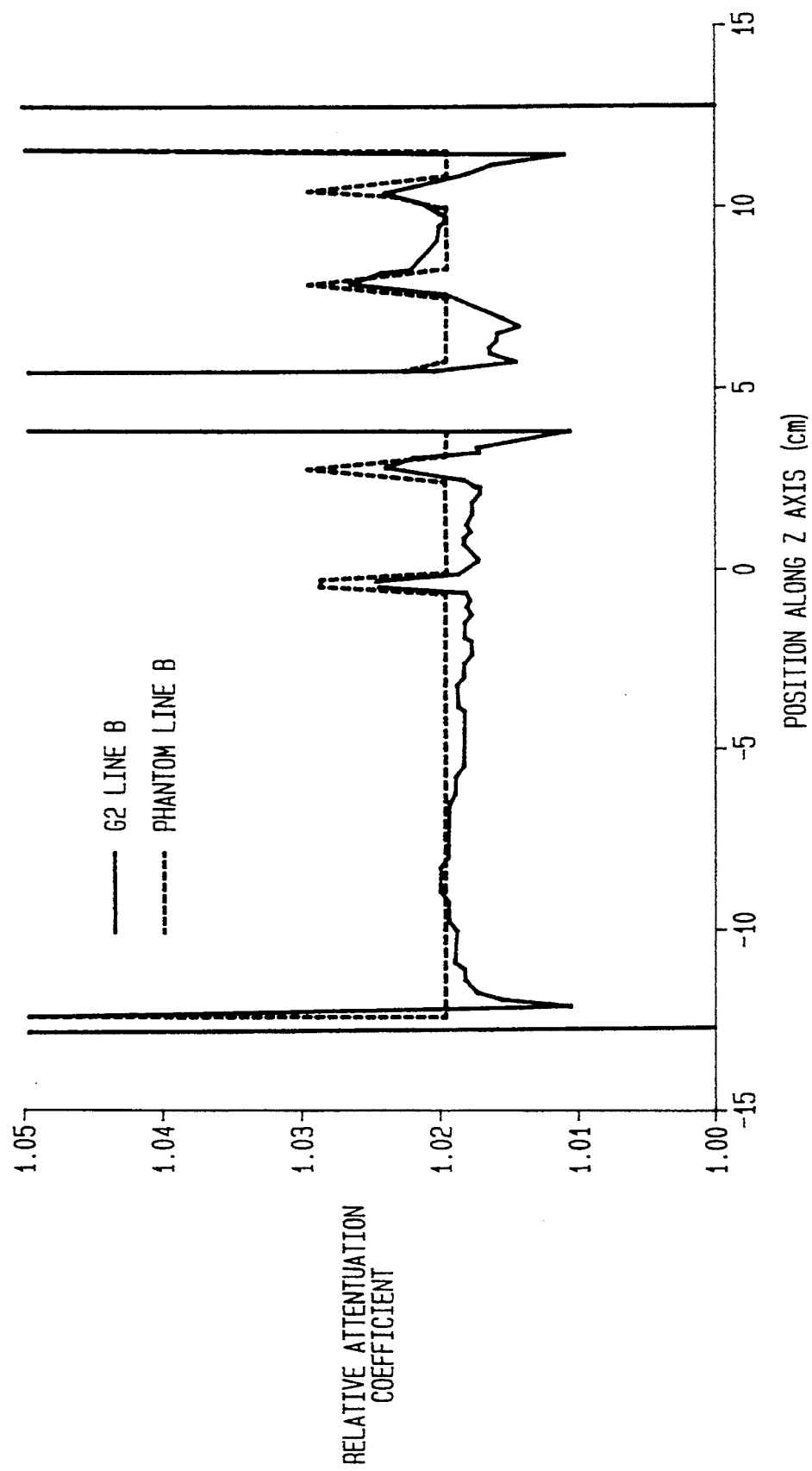

METHOD AND APPARATUS FOR 3-D COMPUTER TOMOGRAPHY

FIELD OF THE INVENTION

The field of the present invention relates generally to x-ray imaging methods and apparatus, and more particularly to computer tomography methods and apparatus for obtaining volume imaging of an object such as a portion of a human body.

BACKGROUND OF THE INVENTION

It is important in both the medical fields, and in industry, to have the ability to non-invasively obtain images of interior portions of various objects, such as human organs, castings, and so forth. Particularly in the medical field, methods and apparatus for providing computer tomography (hereinafter CT) have evolved since about 1974, to relatively sophisticated two-dimensional (2-D) imaging systems. Such 2-D systems typically utilize a fan beam scanning mode for computer reconstruction of 2-D images. At present the most advanced CT devices, such as the Siemens SOMATOM, use a spiralling source—detector assembly and reconstruction is achieved from a series of 2-D slices. It is generally recognized that the next generation of CT devices will have to come from volume real time imaging for making examination possible, for example, of the palpitations of the heart. In order to achieve this, a speed up of both the data collection time and the reconstruction time are necessary. By using the full extent of an x-ray source producing a cone beam, and by using a surface detector such as an Image Intensifier in the Siemens MULTISKOP, data collection can indeed be speeded up significantly. However, a suitable high resolution fast 3-D reconstruction method with a large usable volume has yet to be devised. Although there are good iterative algebraic reconstruction methods which can be made very accurate, they usually take an inordinate amount of computer time to reach convergence.

Modern diagnostic radiology systems permit a radiologist to produce and interpret shadow images of internal organs of a human body, as indicated above. In such systems, x-radiation is used typically having an energy spectrum ranging from 50 to 200 keV, but in an industrial application significantly higher energy ranges may be used. Also in a typical diagnostic x-ray system a relatively broad beam of x-rays are utilized by passing them through an object, such as a section of a human body, whereby the rays exiting from the section of the body are impinged upon a detector. The detector typically may consist of photographic film or an x-ray detection tube. The x-rays are attenuated as they pass through a body, for example, according to the equation $I = I_0 e^{-\mu x}$ where $I_0$ is the intensity of the x-ray beam, $\mu$ is an attenuation coefficient, and x is the thickness of the body. Since the attenuation coefficient $\mu$ is a function of the density of the material through the body and the atomic number thereof, various components of the body respectively attenuate the beam differently at different points as it passes through the body. These varying attenuation components of the x-ray beam exiting the body are detected as varying amounts of radiation. As a result, the detected beam provides a 2-D representation of the attenuation throughout the body.

A detector of photographic film provides a relatively high resolution permanent record or recorded image of the body. The resolution may approach 0.1 mm.

A disadvantage of such known systems is that only a 2-D representation is obtained of a 3-dimensional body.

Computerized tomography or tomographic systems have been developed for transmitting a relatively narrow x-ray beam through the body in a plane perpendicular to the axis of revolution. The detector is used to repetitively measure the total attenuation of the beam, typically thousands of times, with different rays being transmitted through the body in the same plane. Thousands of attenuation measurements are obtained across a narrow slice of a body in a plane perpendicular to the rotation axis. The sum of the attenuation through each of the segments along the beam path are representative of the attenuation of a narrow beam along the path. Accordingly, the total attenuation is equivalent to the sum of the attenuation of each segment.

In practice, for a given body slice being studied, the slices are divided into a plurality of pixels or surface elements. As a result, the attenuation measured at each of the pixels provides a measurement of the attenuation of the narrow beam through the body. Typical grid sizes or meshes of pixels are 512 by 512 matrices, requiring several hundred thousand measurements to be made to reproduce a given slice.

The data processing typically involves calculating the attenuation coefficient for each pixel element. The attenuation coefficients are typically normalized relative to a normalization of 1.0 for water, or some higher number for dense materials as found in bones, calcium for example. The normalization number for the water may be one thousand Hounsfield units, for example. The normalized coefficients are ranked in magnitude in accordance with a given scheme, whereafter a gray scale is assigned to the various computerized attenuation coefficients for displaying the slice on a view screen relative to a gray-scale ranking. As a result, a high resolution image showing small differences in tissue characteristics throughout the body are obtained. Similarly, for an industrial application of CT, other normalization criteria may apply.

In the most recent computerized tomographic systems three-dimensional (3-D) images are produced. Certain of these systems provide 3-D images from a plurality of 2-D slices taken in successive parallel planes. Other systems attempt to fill in gaps of data by using a plurality of 2-D slices obtained from a plurality of parallel planes taken along a first axis, and another plurality of slices of parallel planes taken along an axis perpendicular to the first axis. Regardless, such known systems still suffer from poor resolution as one moves away from a centralized focal point along an axis, due to gaps in the data obtained. Note that detectors other than photographic film are used in such modern systems. These detectors may include either ionization chambers filled with high-density gas, solid-state devices, or image intensifiers, for example.

Typically, in CT apparatus the x-ray source is conical, and a slit is generally put in front to make a fan beam source. For 3-D CT, the full extent of the x-ray source is used producing thus a cone beam. The beam pattern projected from the x-ray source is rotated about an object.

The present inventors recognized that in improving 3-D imaging, it is important to develop a truly 3-D reconstruction algorithm that provides both high resolution and fast reconstruction times. One known 3-D reconstruction algorithm has been developed by Feldkamp et al. (L. A. Feldkamp, L. C. Davis and J. W. Kress, "PRACTICAL CONE BEAM ALGORITHM", *J. Opt. Soc. Am,* 6 June 1984). The Feldkamp et al. algorithm, being basically an extension of the 2-D fan beam backprojection algorithm, is generally recognized by researchers as being very efficient. However, the present inventors discovered that because this algorithm only scans in the midplane, blurred images are produced at large vertical distances from the midplane, and that this deficiency is intrinsic to the scanning method.

Many attempts have been made in the prior art to provide 3-D tomography. For example, in Fencil et al. U.S. Pat. No. 4,875,165, a method for determination of 3-D structure in biplane angiography is described.

It was commonly thought that if one adds together scan data from two great circles that the "fuzziness" contributions of each would be additive, producing even greater fuzziness. The inventors disproved this by using the method of the present invention, whereby by adding together processed scan data from a plurality of great circle scans of an object, they discovered that fuzziness is actually reduced.

SUMMARY OF THE INVENTION

An object of the invention is to provide 3-D CT with high resolution capabilities for a large active volume.

Another object of the invention is to provide 3-D CT systems with the capability of multi scanning in orthogonal planes in a manner substantially eliminating blurring.

Another object of the invention is to provide an improved method for CT volume reconstruction.

In one embodiment, these and other objects are provided in a CT system by scanning in two substantially perpendicular circles using two Feldkamp reconstructions, and adding the data obtained therefrom together. Such scanning results in substantial improvements in resolution relative to known systems. In another embodiment of the invention, a third scan is made substantially perpendicular to the other two scans, for providing symmetrical and complete sampling for obtaining even greater improvements in spatial and contrast resolution.

BRIEF DESCRIPTION OF THE DRAWINGS

Various embodiments of the present invention are described in detail below with reference to the accompanying drawings, in which like items are identified by the same reference designation, wherein:

FIG. 11A shows a diagram of a projection produced by scanning an object in an embodiment of the invention.

FIG. 11B is a simplistic diagram showing a basic Fourier transform of the projection of an object shown in FIG. 11A.

FIG. 11C is a diagram showing a slice in 2-D of the Fourier transform of the projection of the object shown in FIG. 11A in the space domain.

FIGS. 26A and 26B are graphs obtained from the results of computer simulation for showing contrast resolution for 10 HU and 3 HU, respectively.

FIGS. 28A and 28B each show graphs of a section through a simulated coronal plane for phantom and reconstructed planes.

DETAILED DESCRIPTION OF THE INVENTION

Figure 1:
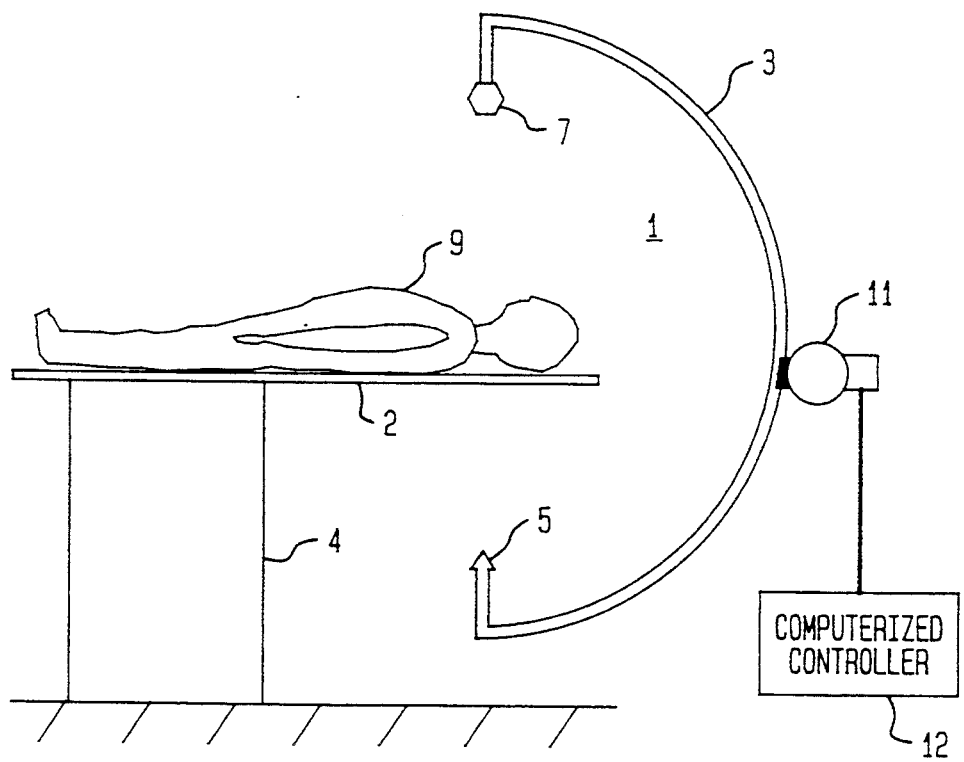
FIG. 1 shows a simplistic pictorial diagram of a known rotational source and detector assembly.

In FIG. 1, a simplified pictorial drawing shows a basic 3-D cone beam computerized tomographic (CT) system 1 that includes a semicircular or "C" arm 3 having an x-ray tube or transmitting device 5 connected at its one end, and an x-ray detecting device 7 mounted upon its other end, as shown. The x-ray tube or transmitter 5 is positioned in direct opposition to and alignment with the x-ray detector 7, thereby permitting x-rays passing through a patient 9 in this example, to be detected by the x-ray detector 7. The arm 3 is held by a gimbal mount 11, for example, for permitting the arm 3 to be positioned in any position within the plane of rotation the x-ray beams from x-ray tube 5 to be transmitted through any of these planes. Also, through use of the gimbal mount 11, in this example, in any given plane the arm 3 can be rotated through about 360°. A computerized controller 12 is included for processing the scanning data received from the detector 7, and for controlling the operation of the x-ray tube 5.

Figure 2:
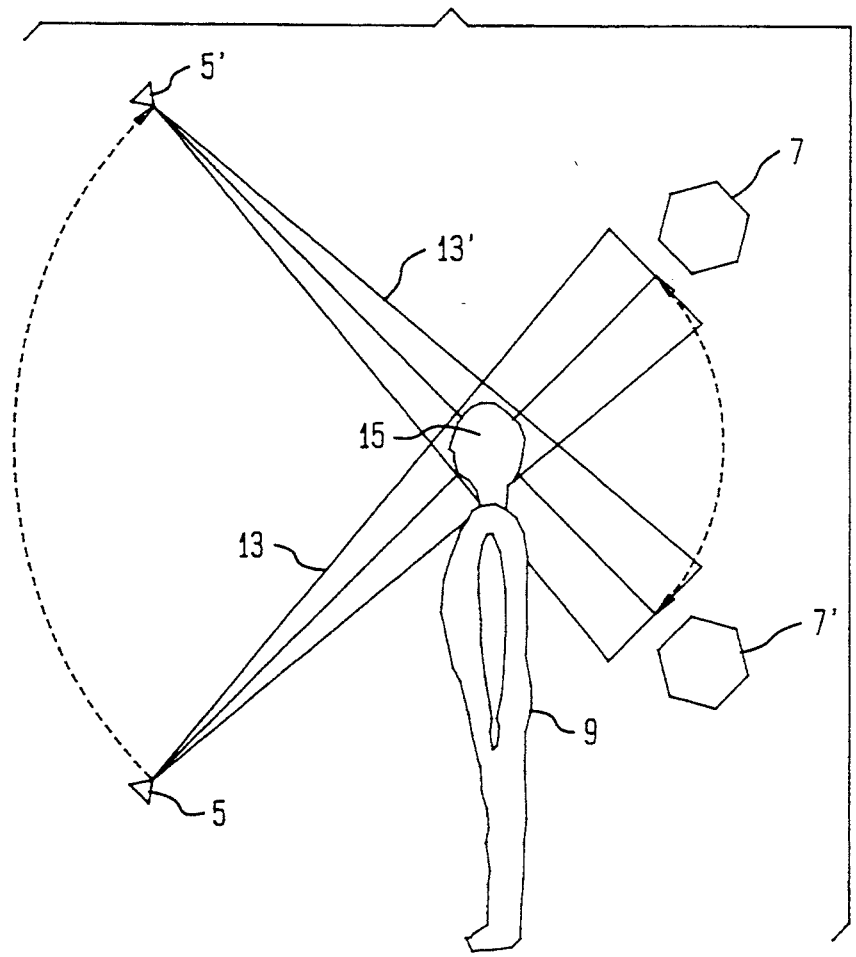
FIG. 2 is a simplistic pictorial drawing showing the relation of a patient to a scanner assembly such as that of FIG. 1, with the assembly being rotated in two orthogonal circles.

As shown in FIG. 2, the x-rays transmitted from the x-ray tube 5 typically are in the form of a cone beam centered in and transmitted through a conical volume 13. In this example, the cone beam is shown passing through the head 15 of a patient 9, whereafter the beam is detected by a detector 7 in a plane perpendicular to the axis of the cone. In conducting a radiology study of a patient 9, the arm 3 of FIG. 1 is typically moved for rotating the x-ray tube 5 and detector 7 in a great circle for obtaining a projected image of the head 15 of the patient 9 in the plane of the detector 7, for example. This is shown pictorially by indicating the end movement in a particular scanning operation showing the repositioning of the x-ray tube 5 and detector 7 to a new rotation plane 13', with the x-ray tube and detector being shown as 5' and 7', respectively, for purposes of illustration. These different positions within the rotation planes described by a circular path provide the necessary data for producing a 3-D image of a portion of the patient's head 15, in this example.

In this standard set-up, the further one moves along the z axis, for example, from the object center, the resolution degrades causing blurring. Thus reducing the viable active volume to a small region about the center of the co-ordinate system.

The present inventors discovered that through use of at least two, and preferably three, orthogonal circles for scanning or movement of the x-ray source 5 and detector 7, that substantial improvement in the resolution for 3-D tomography is obtained. A key consideration, as discussed in greater detail below, is to provide fast algorithms for reducing the computer time required for processing the data obtained to reconstruct the 3-D image.

Figure 3:
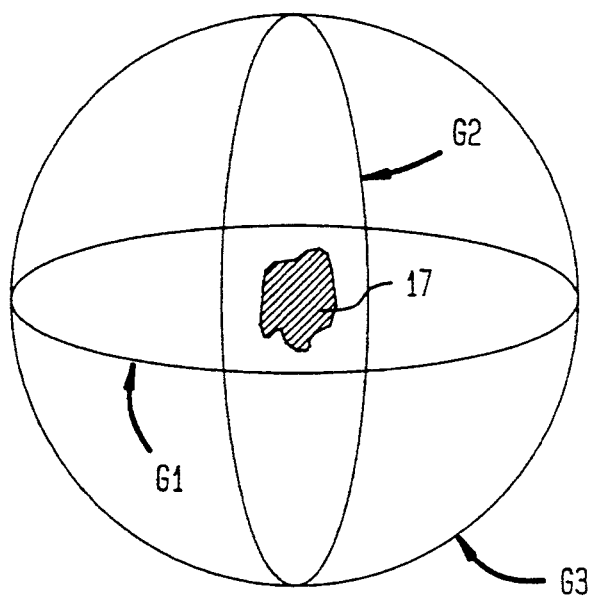
FIG. 3 is a pictorial drawing showing the path of the source or detector in three orthogonal great circles G1, G2, G3, about a centrally located object. This is for showing scanning modes for one embodiment of the invention.

In FIG. 3, three perpendicular or orthogonal great circles $G_1$, $G_2$, $G_3$ are illustrated in a simplistic pictorial diagram for showing how these circles are traced by the vertex of a typical cone beam projected from an x-ray tube 5. As shown, 3-D object 17, such as a patient 9 under study, is located within the center of the circles $G_1$, $G_2$, and $G_3$, respectively.

Figure 4:
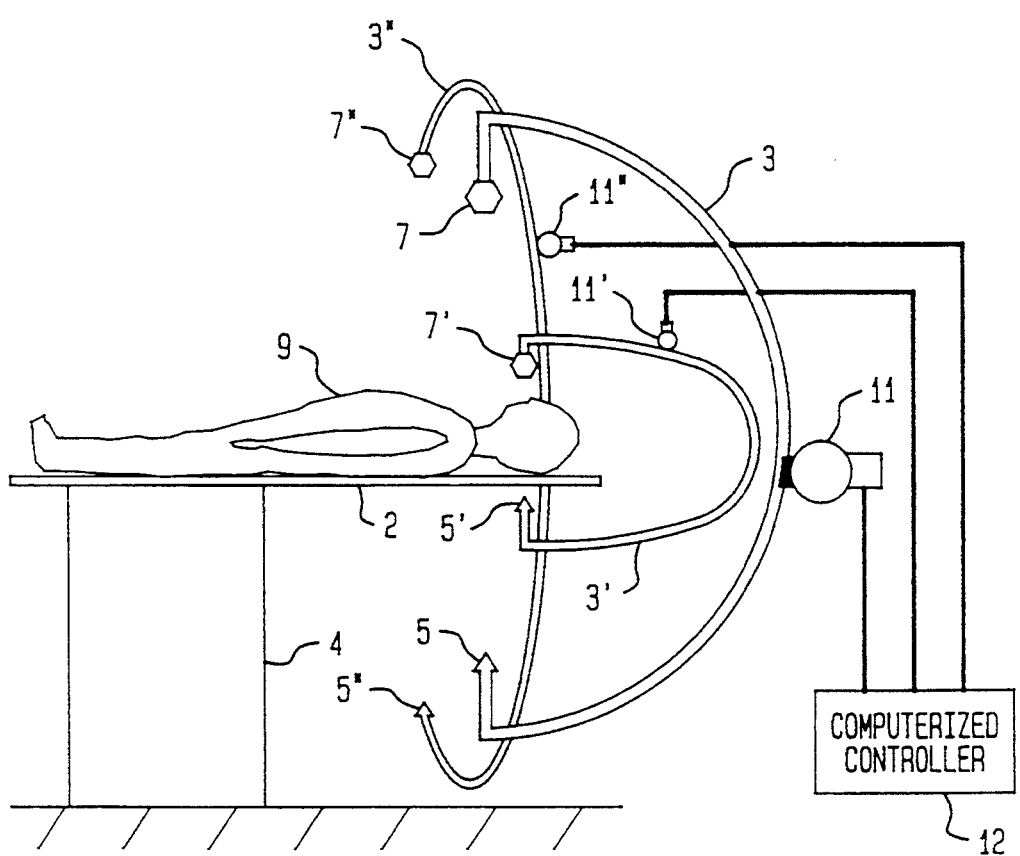
FIG. 4 shows a simplistic pictorial diagram of a computer tomography system including three source-detector assemblies for providing G1, G2, G3 modes of scanning in one embodiment of the invention.

Scanning with the source and detector centers contained within the three perpendicular great circles $G_1$, $G_2$, $G_3$ can be accomplished with present tomographic mechanisms, such as shown in FIG. 1, by moving the arm 3 as required for positioning the x-ray tube 5 and detector 7 in the plane of a desired one of the great circles $G_1$, $G_2$, and $G_3$. Once positioned, the arm 3 would then be moved for rotating the x-ray tube 5 and detector 7 through a plurality of different scanning angles within the associated one of the great circular planes $G_1$, $G_2$, or $G_3$. However, in a practical computerized tomographic system this may prove to be rather time consuming. To provide the required scans in a minimum period of time, a tomographic system could be provided that has three arms 3, 3', 3", and associated x-ray tubes 5, 5', 5", and associated x-ray detectors 7, 7', 7", respectively, as shown in FIG. 4. Note that although the patient 9 is shown in a particular position in FIG. 4 relative to the apparatus, other positions such as placing the patient at 45° to the source and detector assemblies 5, 5', 5" and 7, 7', 7", respectively. Detectors 7, 7', and 7" can each be provided by a two dimensional detector, or a two dimensional array of individual detectors, for example, but are not limited thereto. In this embodiment, the patient 9 is positioned prone upon a table top 2 supported by a pedestal 4, for example. Note that this is not meant to be limiting in any way, in that the patient 9 may be otherwise positioned or examined in a standing position, for example. Note also, that the three orthogonal scanning systems also include gimbal mounts 11, 11', and 11", respectively, with central control being provided by computerized controller 12, in this example. Through the use of two of three orthogonal scans, by this or some other computer topographic system mechanism, symmetric and complete sampling is obtained for providing ultra high spatial and contrast resolution. As previously mentioned, a significant improvement is obtained in resolution relative to single plane scan systems.

A description now follows of the results of various analysis and computer studies relative to developing an algorithm for relative fast processing of the data obtained from the three $G_1$, $G_2$, and $G_3$ scans. The inventors recognized that a method for processing data partly based upon "convolution filtered back projection" appeared practical. Further studies also show that an algorithm proposed by Feldkamp et al. (L. A. Feldkamp, L. C. Davis and J. W. Kress, "Practical Cone Beam Algorithm", *J. Opt. Soc. Am*, 1, Jun. 6, 1984) which is applicable to the single scanning circle configuration of FIG. 1 appears to be amongst the fastest of algorithms for computer execution.

In order to better understand the invention, a survey of volume reconstruction is described below. This is followed by a description of the algorithm or algorithms required for a processing the data obtained from the three scans in the preferred embodiment in the present invention.

Figure 5:
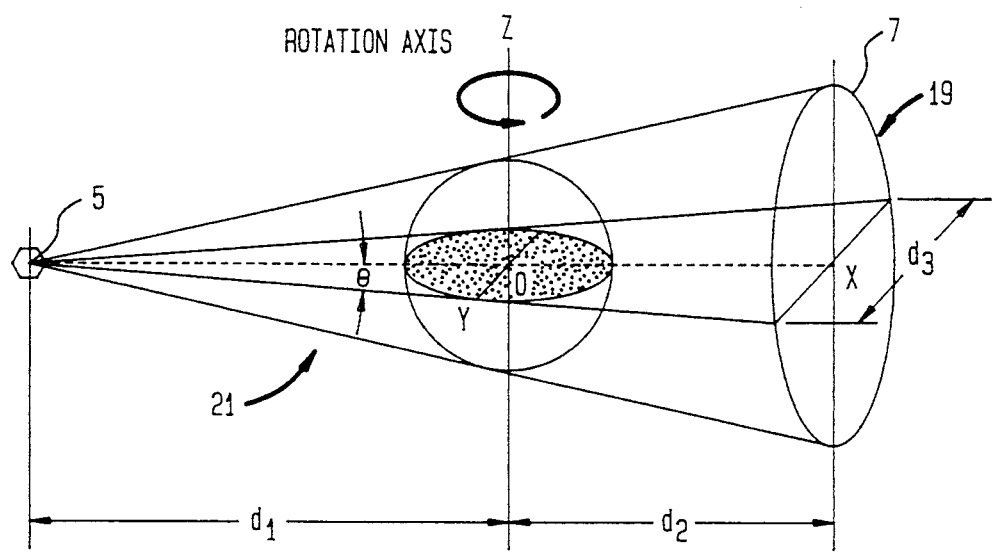
FIG. 5 is a schematic diagram showing the geometry of an experimental CT system.

In FIG. 5, the geometry of a volume reconstruction is shown, for example. Assume that a source 5 and a two dimensional detector 7 are rotated in the x-y plane about the z axis, the latter being the rotation axis. The distance $d_1$ between the source 5 and rotation axis z is assumed to be 70 centimeters in this example, whereas the distance $d_2$ between the z axis and the detector plane 19 is assumed to be 30 centimeters. In this example, the detector 7 is assumed to be an Image Intensifier 7 having a diameter $d_3$ of 40 centimeters. Accordingly, the active volume of reconstruction is a sphere of radius $d_1 \sin \theta$, where $\theta$ is the cone beam 21 half angle. Also, $\theta$ is approximately 11°, whereby $d_1 \sin \theta$ is approximately 13.7 centimeters, for example.

Figure 6:
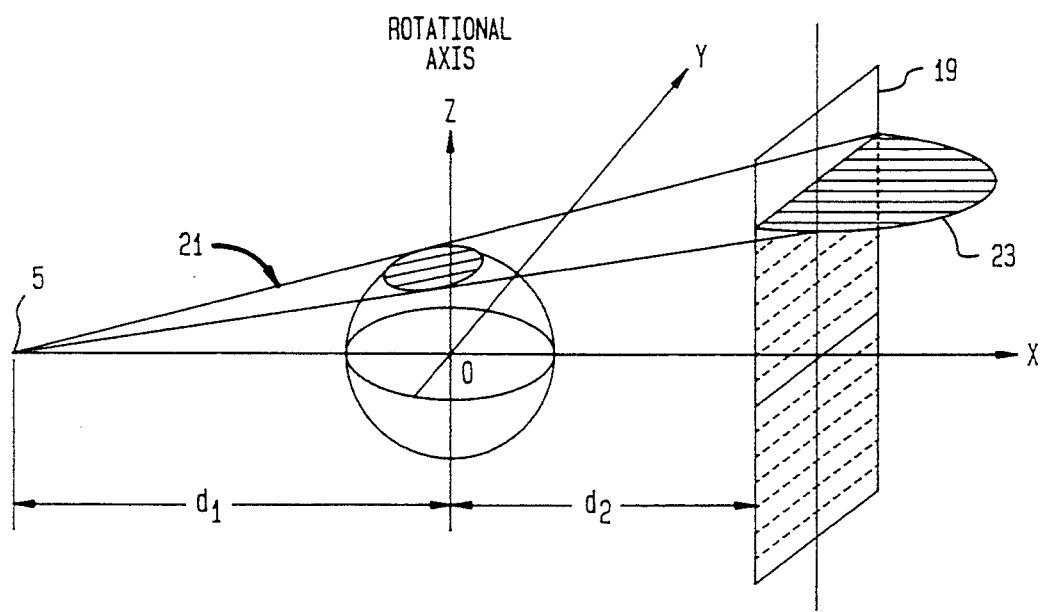
FIG. 6 is a schematic diagram illustrating the geometry used in Feldkamp reconstructions associated with various embodiments of the invention.
Figure 7:
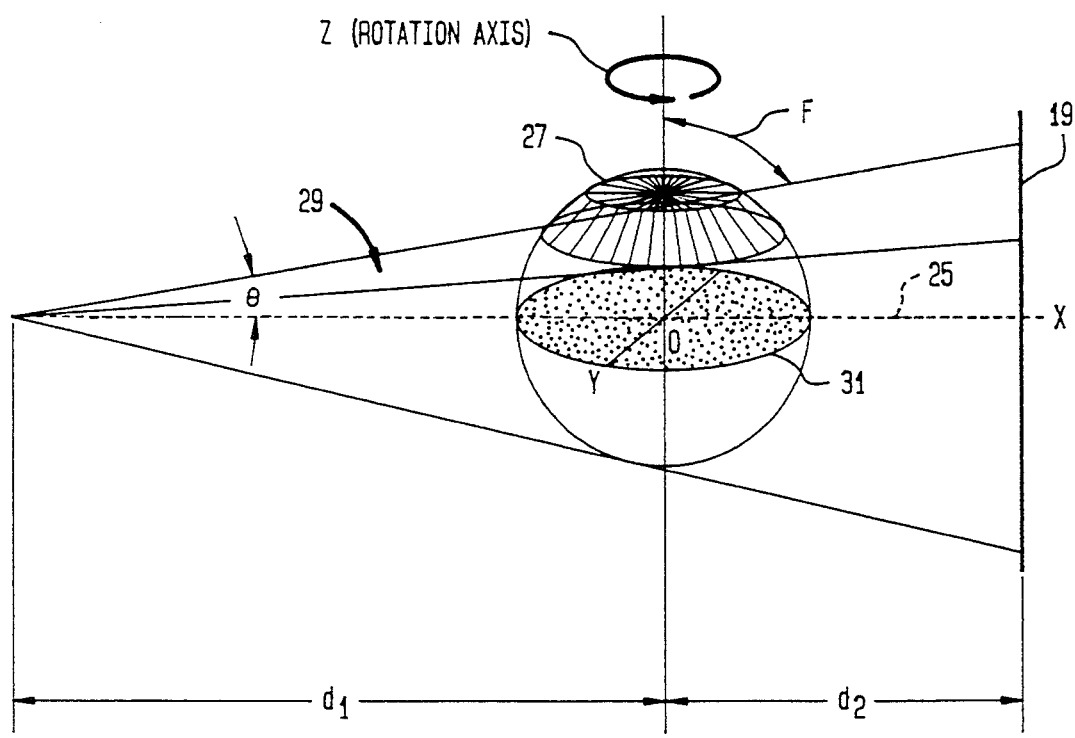
FIG. 7 is a schematic diagram showing cones traced out by the midline of a tilted plane as a source and detector assembly are rotated around an object, relative to an embodiment of the invention.

The Feldkamp algorithm makes use of the fan beam algorithm in a set of tilted planes whose normals 23 are tilted out of the z direction, as shown in FIG. 6. As the source 5 and detector 7 assembly rotates, a line 25 down the middle of a tilted plane traces out a shallow cone 27, as shown in FIG. 7. The highest of such shallow cones 27 has a half angle F of $(\pi/2-\theta)$. For tilted planes 29 which intersect the z axis at lower z values, the cone angle becomes progressively larger until at midplane it is equal to $\pi/2$. As a result, it is important to note that for such a single scan a large amount of data is missing, or unsampled. Given mesh points (points in a sampling grid) do not lie on a cone as the source 5 is rotated, but oscillate up and down over several cones, with the oscillation being larger for higher z values. As a result, the values to be back projected must be obtained by interpolation in the y-z projection plane. On the midplane 31, the Feldkamp algorithm reduces to a normal fan beam algorithm, requiring no interpolation, thereby yielding good results. However, for planes at large z values image data is not accurately reproduced. To maintain reasonable accuracy, the cone beam half angle $\theta$ should be less than 10°. Through use of the distance measurements given in the present example, it is then expected that a good or accurate reconstruction region can be obtained for a sphere of radius of at least 13 centimeters.

Figure 8:
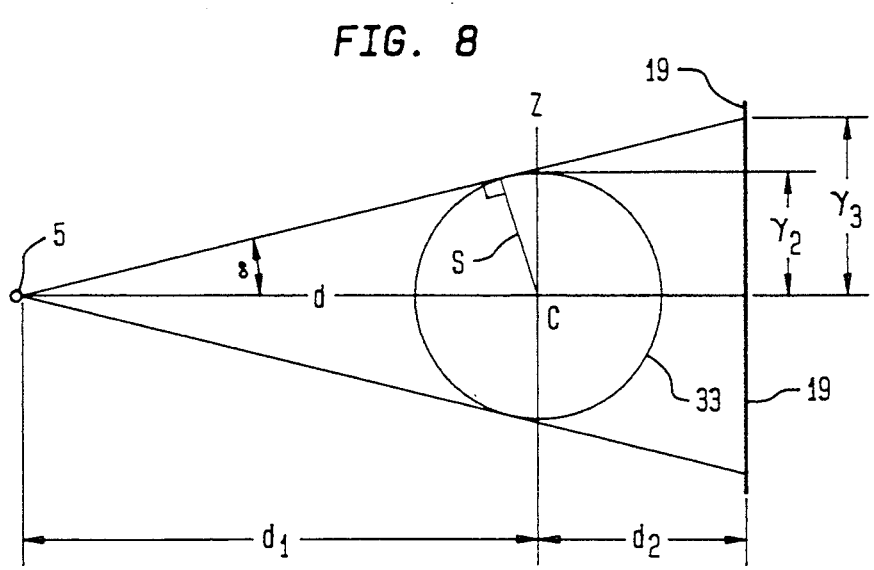
FIG. 8 is a schematic diagram showing derivation of an active reconstruction volume.
Figure 9:
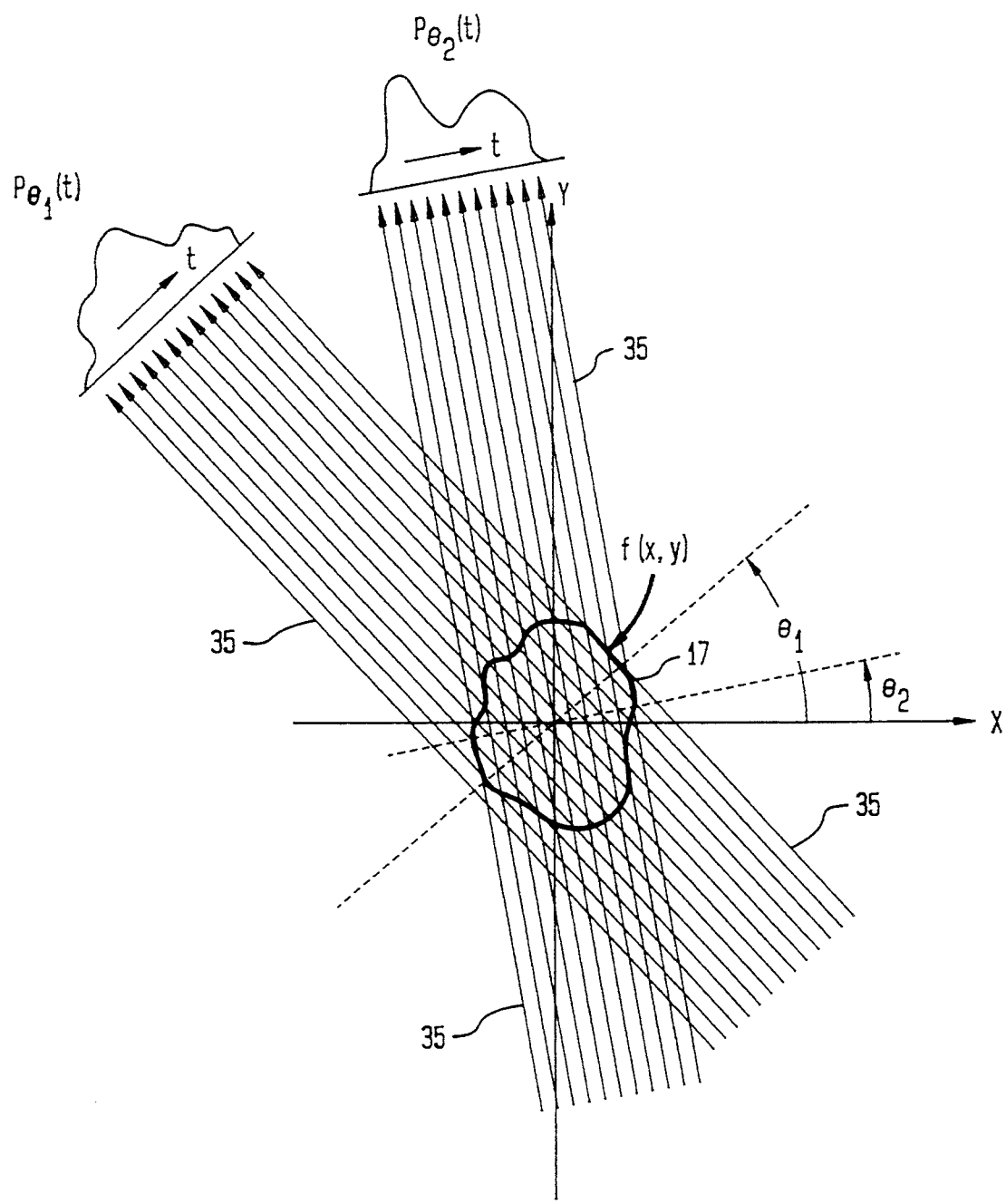
FIG. 9 is a schematic diagram showing the basic principle of a CT reconstruction method.
Figure 10:
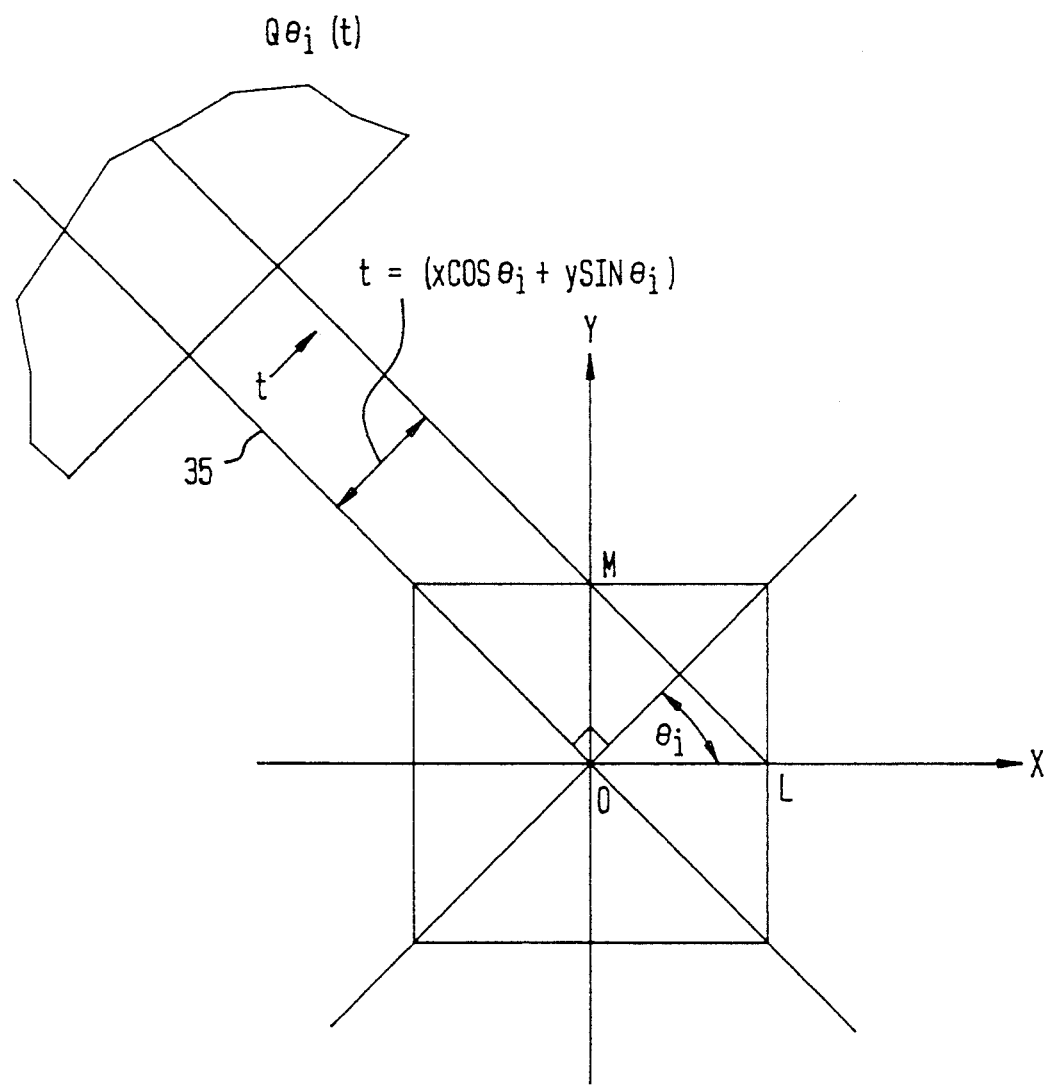
FIG. 10 is a schematic diagram for illustrating the definition of Radon parameters.
Figure 12:
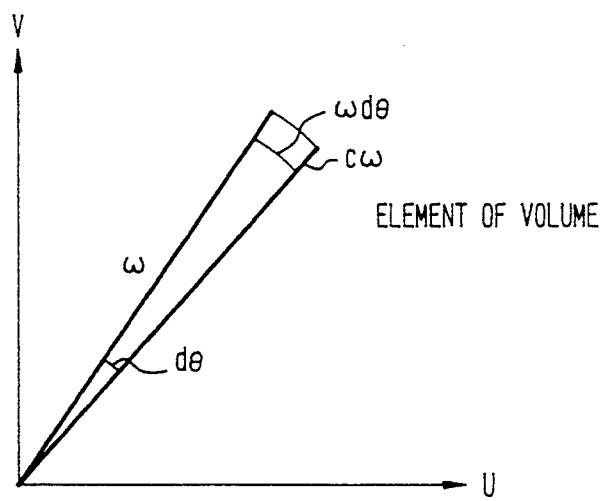
FIG. 12 is a diagram showing an element of area in Fourier space.
Figure 13:
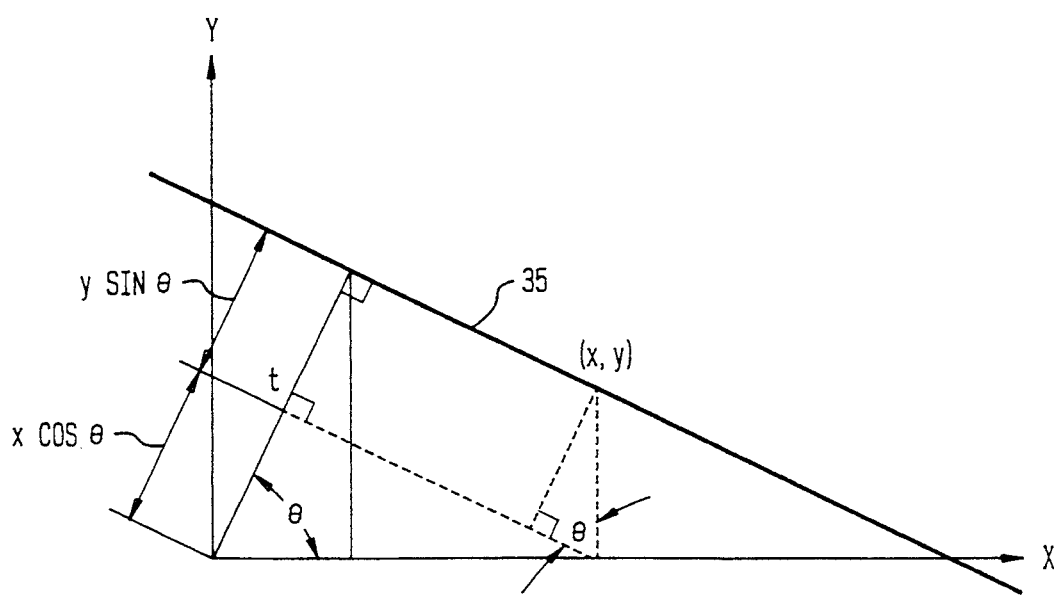
FIG. 13 is a pictorial diagram showing the geometric proof of $t = x\cos\theta + y\sin\theta = $ constant along a projection line.
Figure 14:
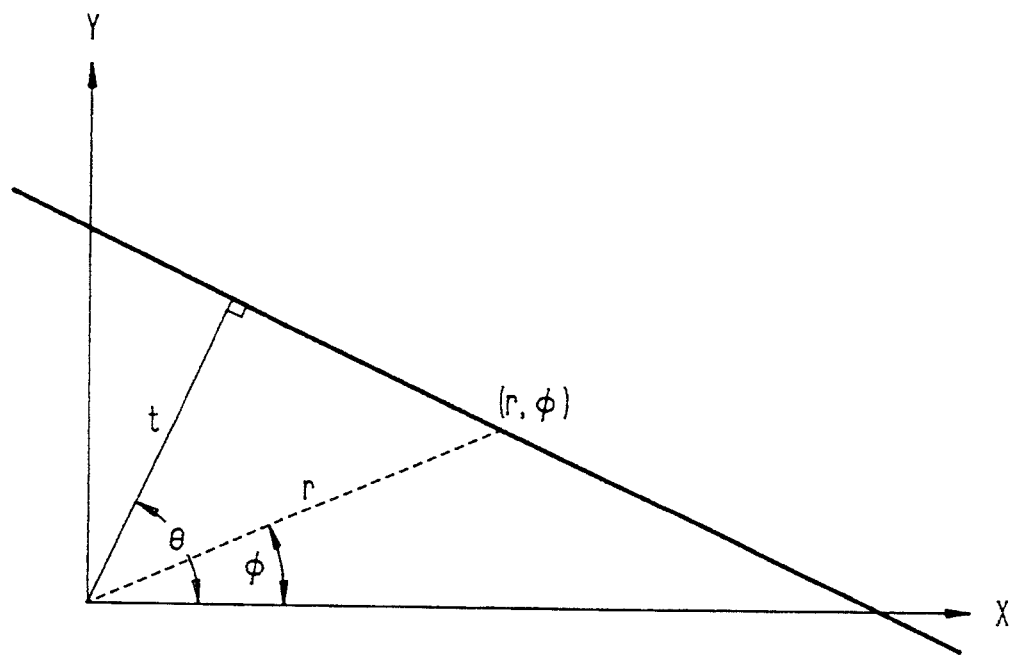
FIG. 14 is a pictorial diagram showing a Radon parameter t of a point on a projection line in cylindrical coordinates.

The derivation of an active reconstruction volume will now be discussed with reference to FIG. 8. In this example, assuming that the diameter for the image intensifier or detector 7 is 40 centimeters, then the radius will therefore be 20 centimeters, which is divided into 220 pixels. This radius is reduced to 14 centimeters when projected back to a plane 33 including the rotation axis z. Further calculation, relative to FIG. 8, shows that the active radius of reconstruction s is 13.7 centimeters. The number of pixels is zero (0) padded to (256), as required for the fast Fourier transform, thereby effectively providing a detector plane mesh of (256×256) with a spacing of 0.13 centimeter when projected back onto a plane 33 including the rotation axis z. For the 3-D object 17 or patient 9 under observation, a mesh of (140×140×140) with a spacing of 0.19 centimeters is used, centered about the center of the co-ordinate system C. Thus the active volume is just contained within the 3-D mesh. The reconstruction procedure then consists of transforming each projection into Fourier space, multiplying by a ramp function and a Hamming window function, taking an inverse Fourier transform, and then back projecting using bilinear interpolation in the two dimensional mesh of filtered convolution values.

The operation of the present invention will not be described as based upon a Feldkamp algorithm. Although a mathematical presentation is given below, the physical phenomena under consideration is stressed and described in conjunction with the mathematical explanation. The explanation follows below with specific subject headings.

I. The Feldkamp Reconstruction Algorithm

The basic equation for fan beam reconstruction can be written as equation (1) which is known to those skilled in the art. It is shown in "Principles of Computerized Tomographic Imaging" by Kak and Slaney, published by *IEEE Press*, 1988 (IEEE Order No. PC02071), at page 104, equation 163, incorporated by reference herein.

$$f(r,\phi) = \int_0^{2\pi} \frac{1}{U^2} \int_{-p_m}^{p_m} R_\beta(p) \, h(p'-p) \frac{D}{\sqrt{d^2+p^2}} \, dp \, d\beta \quad (1)$$

Figure 17:
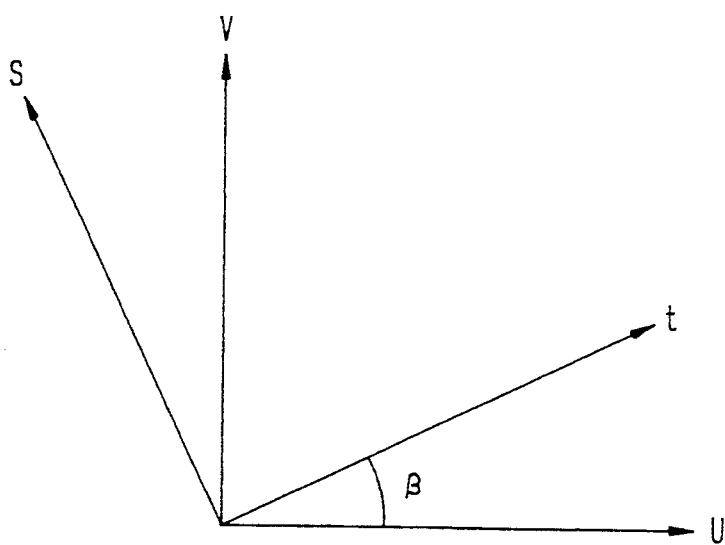
FIG. 17 is a diagram showing the relationship of rotated coordinates (t,s) to the original (x,y) coordinates.
Figure 15:
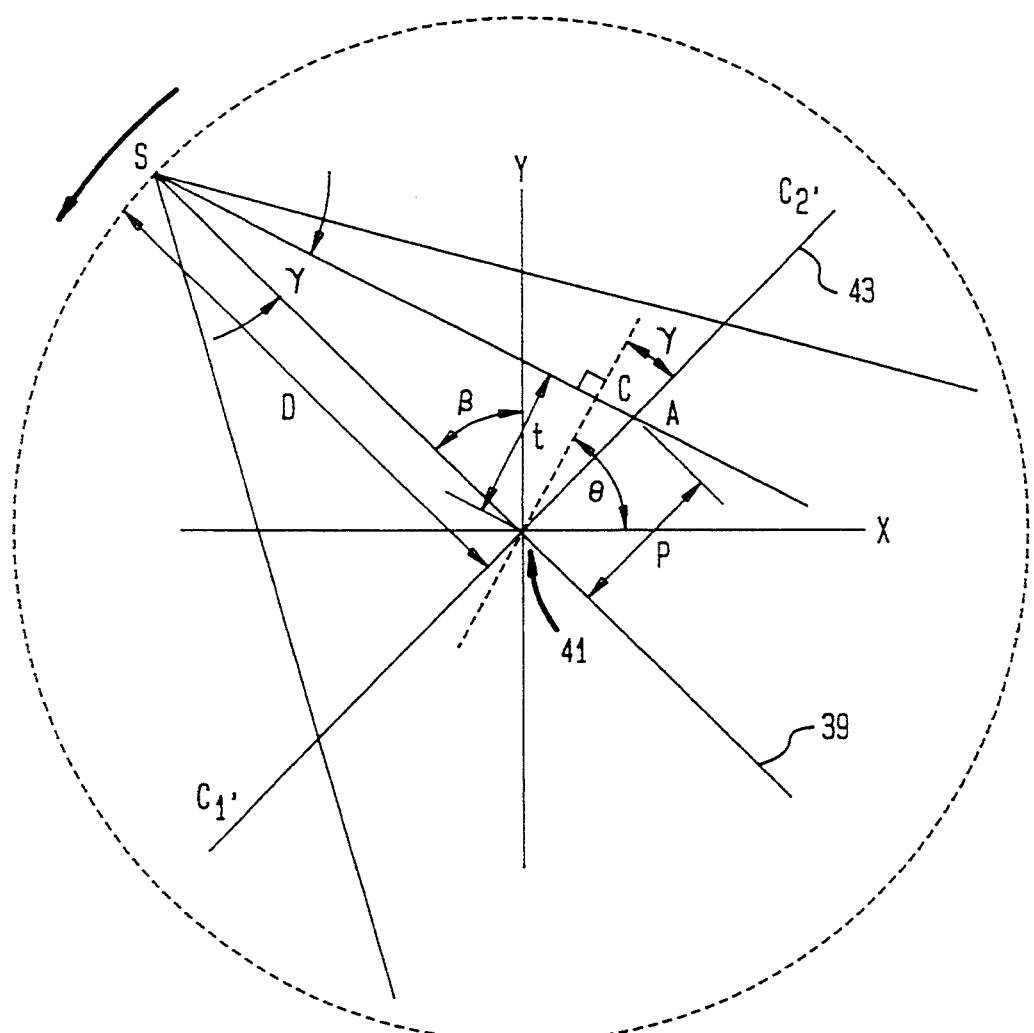
FIG. 15 is a diagram showing the basic geometry of fan beam reconstruction.
Figure 16:
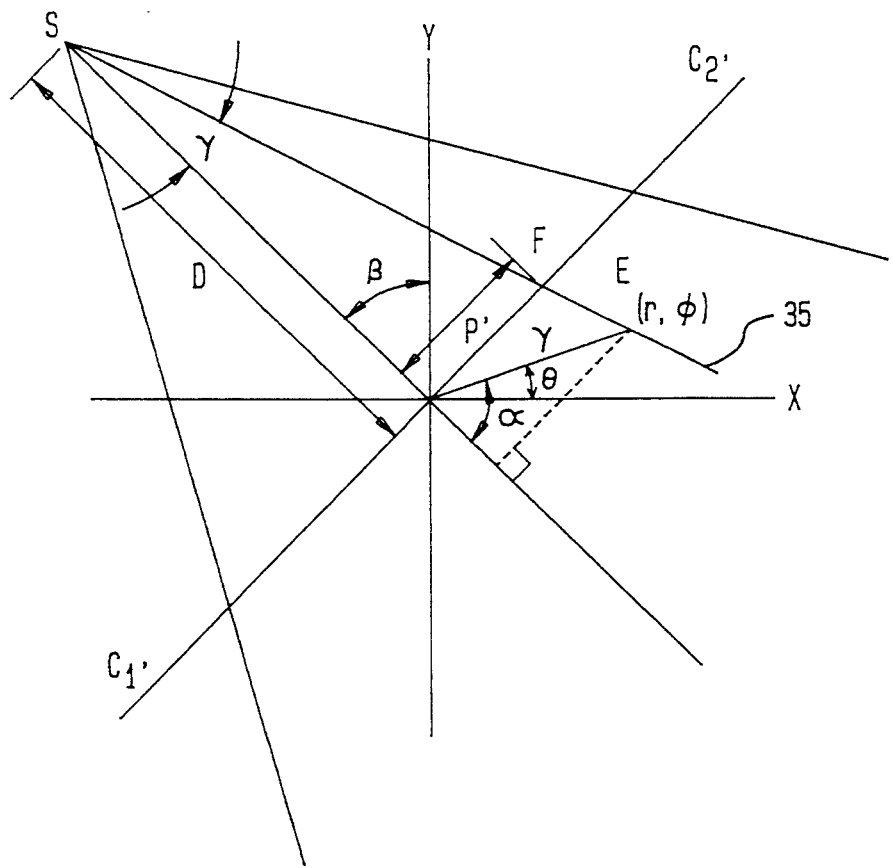
FIG. 16 is a diagram showing parameters of fan beam reconstruction.

Derivation of the cone beam equation:

The Feldkamp algorithm essentially applies the fan beam equation (1) to tilted planes above and below the midplane (horizontal plane) so as to produce a set of projections in the detection plane which rotates with the source 5 around the object 17. The final three-dimensional reconstruction is obtained by summing the set of projections. The cylindrical coordinates $(r,\phi)$ of the previous section will be replaced by a Cartesian system $(t,s)$ which rotates about the z axis with the source and differs from $(x,y)$ by the source angle $\beta$ (see FIG. 17). Accordingly:

$$x = r\cos\phi \quad (2)$$
$$y = r\sin\phi$$

$$\begin{bmatrix} t \\ s \end{bmatrix} = \begin{bmatrix} \cos\beta & \sin\beta \\ -\sin\beta & \cos\beta \end{bmatrix} \begin{bmatrix} x \\ y \end{bmatrix}$$

Figure 18:
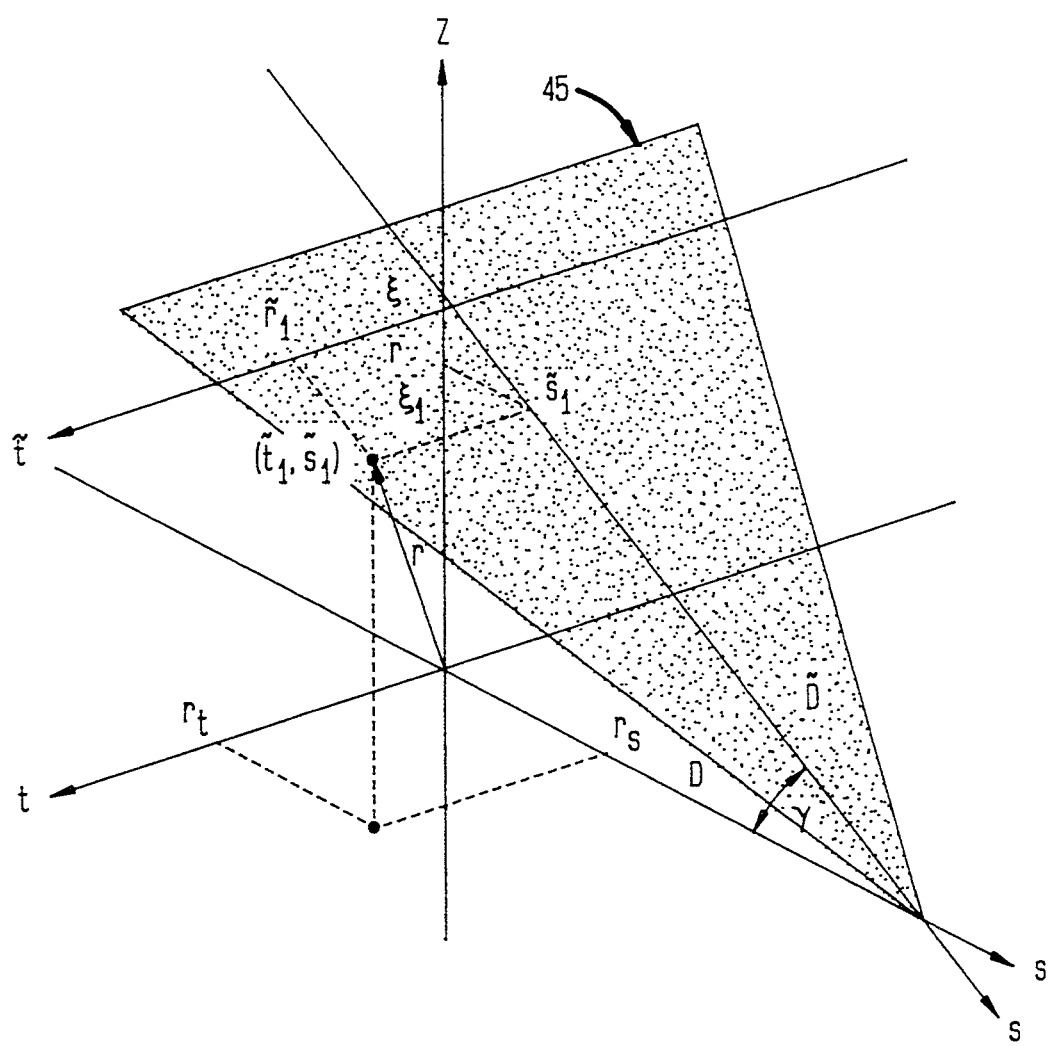
FIG. 18 is a schematic diagram showing the geometry of a tilted plane.

A tilted plane 45 is described by the coordinates $(\tilde{t},\tilde{s})$ (see FIG. 18). This plane contains the source point at $s=D$, $z=0$, but intercepts the z axis at $z=\xi$ at which level a projection is formed along the $\tilde{t}$ axis. Writing the fan beam equation (1) in terms of $(t,s)$ gives:

$$g(t,s) = \int_0^{2\pi} \frac{D^2}{(D-s)^2} \int_{-\infty}^{\infty} R_\beta(p) \, h\left(\frac{Dt}{D-s} - p\right) \frac{d}{\sqrt{D^2+p^2}} \, dp \, d\beta \quad (3)$$

where:

$$\frac{p'}{D} = \frac{t}{D-s} \quad (4)$$

$$U(x,y,\beta) = \frac{D-s}{D} \quad (5)$$

Figure 19:
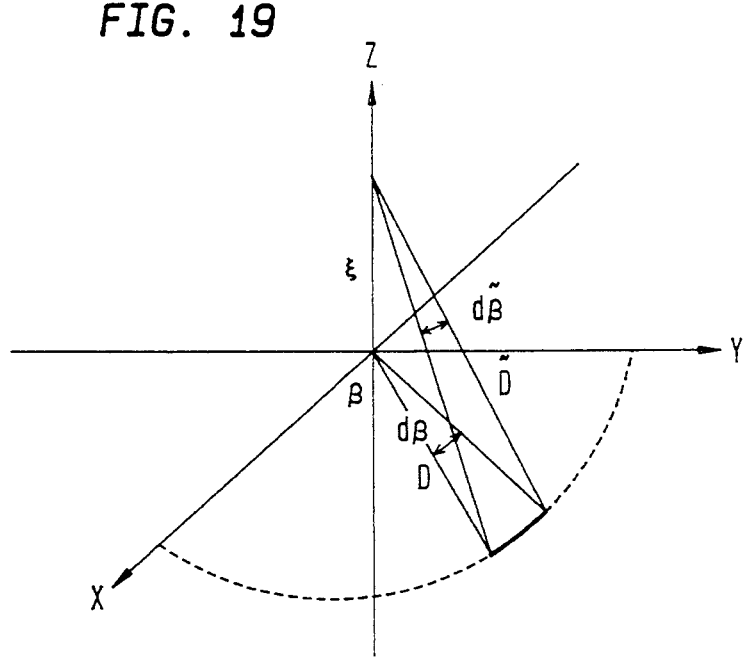
FIG. 19 is a diagram showing the relationship between angles subtended by a detector in the midplane and a tilted plane.

To apply this equation to the tilted plane, several parameters have to be redefined. The new source s to axis distance $\tilde{D}$ is:

$$\tilde{D}^2 = D^2 + \xi^2 \quad (6)$$

and the angle subtended by the detector is now $d\tilde{\beta}$ (FIG. 19) and:

$$d\tilde{\beta} = \frac{D \, d\beta}{\tilde{D}} = \frac{D \, d\beta}{\sqrt{D^2+\xi^2}} \quad (7)$$

Writing $\tilde{D}$ for D, $d\tilde{\beta}$ for $d\beta$ and the projection as $R_{\tilde{\beta}}(p, \xi)$ provides:

$$g(\tilde{t},\tilde{s}) = \int_0^{2\pi} \frac{\tilde{D}^2}{(\tilde{D}-\tilde{s})^2} \int_{-\infty}^{\infty} R_{\tilde{\beta}}(p,\xi) \cdot \qquad (8)$$

$$h\left(\frac{\tilde{D}\tilde{t}}{\tilde{D}-\tilde{s}} - p\right) \frac{\tilde{D}}{\sqrt{\tilde{D}^2 + p^2}} dp \, d\tilde{\beta}$$

Figure 20A:
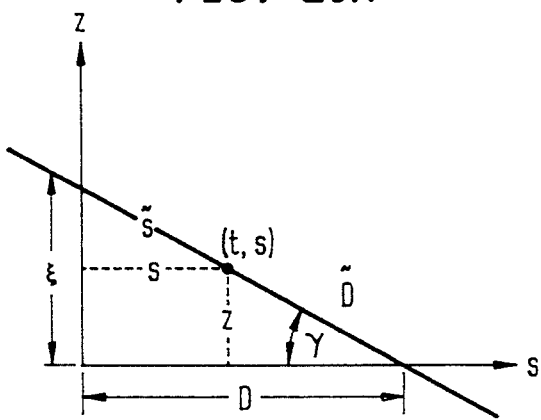
FIGS. 20A and 20B are diagrams showing the relationship between midplane and tilted plane variables.
Figure 20B:
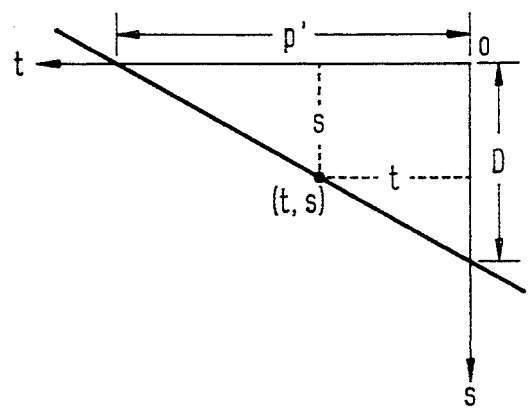

This equation has to be written in terms of (t,s) requiring the following relations (see FIGS. 20A and 20B):

$$\tilde{t} = t \qquad (9)$$

$$\tilde{s} = \frac{sD}{D} \qquad (10)$$

$$\xi = D \tan\gamma = \frac{z}{D-s} \qquad (11)$$

$$\frac{\tilde{D}^2}{(\tilde{D}-\tilde{s})^2} = \frac{D^2}{(D-s)^2} \qquad (12)$$

$$\frac{\tilde{D} \, d\tilde{\beta}}{\sqrt{\tilde{D}^2 + p^2}} = \frac{D^2 + \xi^2}{\sqrt{D^2 + \xi^2 + p^2}} \cdot \frac{D \, d\beta}{D^2 + \xi^2} \qquad (13)$$

$$= \frac{D \, d\beta}{\sqrt{D^2 + p^2 + \xi^2}}$$

The equation for cone beam reconstruction is therefore:

$$g(t,s) = \int_0^{2\pi} \frac{D^2}{(D-s)^2} \int_{-\infty}^{\infty} R_{\beta}(p,\xi) \cdot \qquad (14)$$

$$h\left(\frac{Dt}{D-s} - p\right) \frac{D}{\sqrt{D^2 + \xi^2 + p^2}} dp \, d\beta$$

It is clear that if $\tilde{D}=D$ and $\xi=0$ then this equation reduces to the fan beam equation (3).

II. Computer Implementation

1. Implementation of the Feldkamp algorithm
The procedure may be summarized as follows:
i) Multiply projection data $R_{62}(p,\xi)$ with weight factor.

$$R_{\beta}'(p,\xi) = \frac{D}{\sqrt{D^2 + \xi^2 + p^2}} R_{\beta}(p,\xi) \qquad (15)$$

ii) Convolve weighted projections $R_{\beta}'(p,\xi)$ with a ramp filter h(p) and a window function H(p), here * denotes a convolution:

$$Q_{\beta}(p,\xi) = R_{\beta}'(p,\xi) * h(p) * H(p) \qquad (16)$$

iii) Backproject a value which is bilinearly interpolated from a grip of $Q_{\beta}(p,\xi)$ values:

$$g(t,s,z) = \int \frac{D^2}{(D-s)^2} Q\left(D\frac{t}{D-s}, D\frac{z}{D-s}\right) d\beta \qquad (17)$$

and then sum up contributions at all source angles $\beta$.

Figure 21:
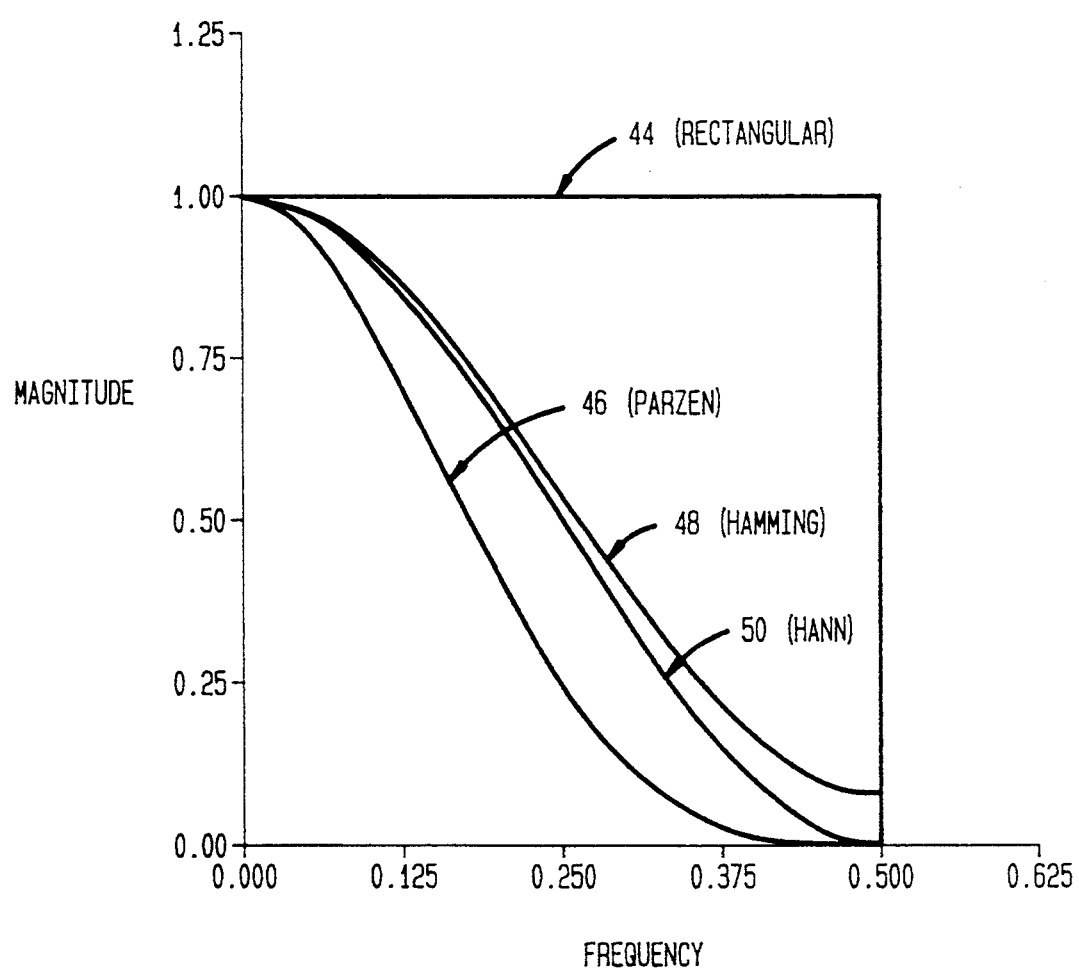
FIG. 21 shows curves relative to window functions in Fourier space.
Figure 22A:
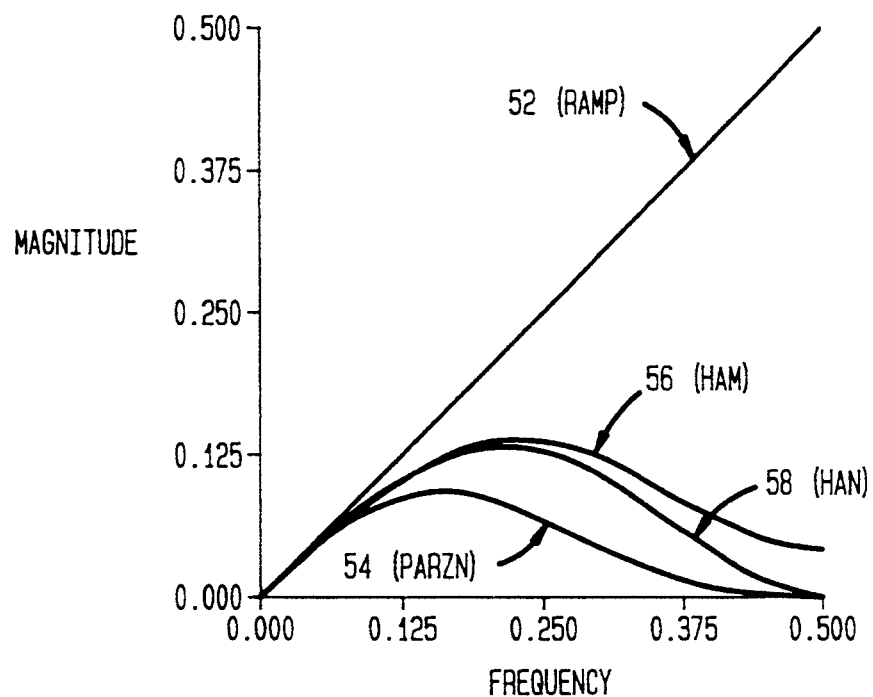
FIGS. 22A and 22B show curves of window filters in Fourier space and in physical space, respectively.
Figure 22B:
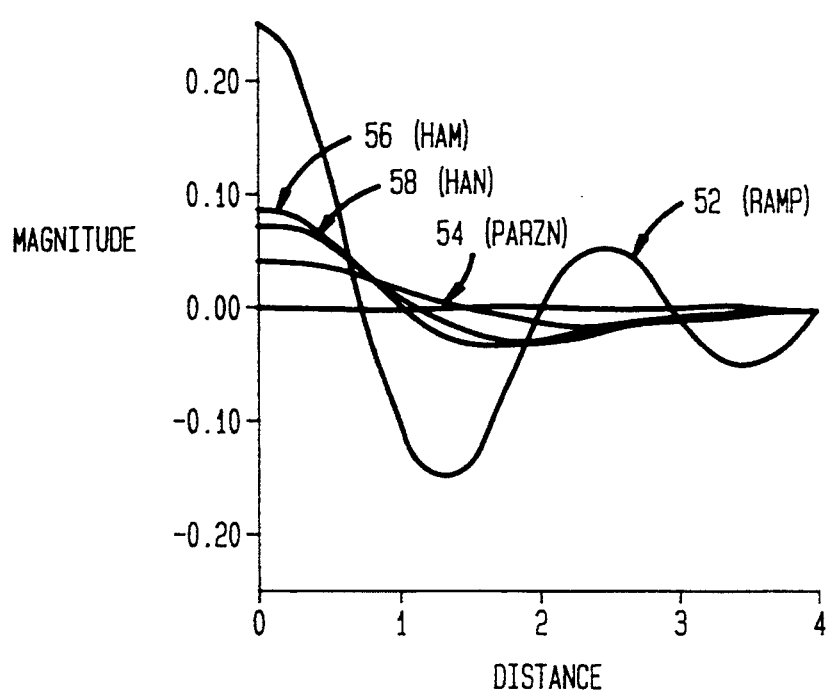

2. Convolution and filtering
Step "ii" for the preceding section is performed in Fourier space for two reasons: First, convolution involves simple multiplication in Fourier space hence it is simple for programming and fast in execution. Second, it is convenient to introduce a frequency dependant filter at this point to suppress high frequency noise in data. The inventors implemented a number of windows which are shown in FIGS. 21 and 22A in Fourier space, and in FIG. 22B in physical space. These window functions, as shown in FIG. 21 include rectangular 44, Parzen 46, Hamming 48, and Hann 50. The window filters response curves resulting from the product of the window functions and a ramp filter, include as shown in FIG. 22A in Fourier space, and FIG. 22B in physical space, ramp 52, Parz 54, Ham 56, and Han 58, respectively. The preferred window is the Hamming window $\tilde{H}$ which is in Fourier space:

$$\tilde{H}(v) = 0.54 + 0.46 \cos\left(\pi \frac{v}{v_m}\right) \qquad (18)$$

if $|v| \leq v_m$ and $\tilde{H}(v)=0$ if $|v|>v_m$. Here $v_m$ is the normalized cutoff frequency; since the output of FFT is in the range $-\pi$ to $\pi$, $v_m$ is equal to 0.5. In this code, the Hamming window is multiplied with the ramp filter to give the Ham filter $\tilde{H}_r$ which is in Fourier space:

$$\tilde{H}_r(v) = 0.54 |v| + 0.46 |v| \cos\left(\pi \frac{v}{v_m}\right) \qquad (19)$$

if $|v| <= v_m$ and $\tilde{H}_r=0$ if $|v|>v_m$. This filter has definitely been found to be effective against artifacts.

3. G1 phantom simulation
Providing a good phantom in the simulation of computer tomography (CT) reconstruction is an integral and important part of the whole computational process. The projection calculated from the line integrals of attenuation along the ray path should not contribute to the final error of the reconstruction; in other words, the error involved in calculating the line integral should be much smaller than that of CT reconstruction. This is particularly important when using iterative schemes where the convergence criterion is formed from the difference between the observed projection and the calculated line integrals from the solution at that stage of the computation. Calculating the projections is also computer time consuming, therefore it is not easy to achieve both speed and accuracy.

The inventors determined that to simplify the algebra only ellipsoids should be employed. Furthermore, they chose to eliminate any additional parameters for orientation since the major and minor radii are substantially the only variables needed for purposes of analysis. This greatly simplifies the algebra and increases the computing speed. An ellipsoid in Cartesian coordinates (x,y,z) is written as:

$$\left(\frac{x-x_0}{A}\right)^2 + \left(\frac{y-y_0}{B}\right)^2 + \left(\frac{z-z_0}{C}\right)^2 = 1 \qquad (20)$$

where $(x_0,y_0,z_0)$ are the coordinates of the center of the ellipsoid and A,B,C give the major and minor axes along the coordinate axes. Start with a large ellipsoid of attenuation relative to water $\mu=2.0$ and another slightly smaller one of $\mu=-0.98$. Thus the result is a skull-like shell of $\mu=2.0$ within which there is a region of soft tissue of $\mu=1.02$. One can study the resolution and artifacts by superimposing a set of small ellipsoids with varying attenuations at different locations inside the skull. To calculate line integrals traversing a group of ellipsoids at any angle can be quite tedious if sufficient care is not taken to optimize the computation by finding the best coordinate system to work in. It is best to keep the source on the x axis for all times, that is at $U(-d,0,0)$ and the detector plane in the (y,z) plane. A point in the detector plane would be at $V(0,y_d,z_d)$. To simulate the scan, the ellipsoids are rotated by an angle $-\beta$, where $\beta$ is the source angle for a source 5, for example. For the contribution of a given ellipsoid to a given projection line, a line is drawn joining U and V, and the intersections of this line with the ellipsoid are determined. The parametric representation for a line passing through two points $(x_1,y_1,z_1)$ and $(x_2,y_2,z_2)$ is as follows:

$$x = x_1 + at \quad (21)$$
$$y = y_1 + bt \quad (22)$$
$$z = z_1 + ct \quad (23)$$

$$t_0 = \sqrt{(x_2 - x_1)^2 + (y_2 - y_1)^2 + (z_2 - z_1)^2} \quad (24)$$

$$a = \frac{x_2 - x_1}{t_0} \quad (25)$$

$$b = \frac{y_2 - y_1}{t_0} \quad (26)$$

$$c = \frac{z_2 - z_1}{t_0} \quad (27)$$

Applying this to U and V results in the following:

$$x = -d + d \frac{t}{t_0} \quad (28)$$

$$y = y_d \frac{t}{t_0} \quad (29)$$

$$z = z_d \frac{t}{t_0} \quad (30)$$

Assume a coordinate system $(x',y',z')$ which is rotated by $-\beta$ about the z axis from the $(x,y,z)$ system. In the ' system the ellipsoid is written as:

$$\left(\frac{x' - x_0}{A}\right)^2 + \left(\frac{y' - y_0}{B}\right)^2 + \left(\frac{z' - z_0}{C}\right)^2 = 1 \quad (31)$$

Since $$\begin{bmatrix} x' \\ y' \end{bmatrix} = \begin{bmatrix} \cos\beta & -\sin\beta \\ \sin\beta & \cos\beta \end{bmatrix} \begin{bmatrix} x \\ y \end{bmatrix} \quad (32)$$

providing:

$$\left(\frac{x\cos\beta - y\sin\beta - x_0}{A}\right)^2 + \left(\frac{y\sin\beta + y\cos\beta - y_0}{B}\right)^2 + \left(\frac{z - z_0}{C}\right)^2 = 1 \quad (33)$$

By substitution into equation (33), and into equations (28)–(30) for the line, one obtains a quadratic in t. The two values of t represent the two intercepts. Finally, intercepts from all ellipsoids on this line have to be sorted along t before calculating the successive attenuations along the entire path.

4. Backprojection

For any given mesh point one must sum the contributions derived by interpolation from the detector plane over all source angles. Therefore it is required to determine the line joining the source to the mesh point, and to find where it intercepts the detector plane. Again it is much more convenient to take the source at $(-d,0,0)$ and detector plane in the (y,z) plane at x=0. The given mesh point (x,y,z) has to be rotated by $\beta$ to be in the system where the source is on the x axis. Therefore:

$$\begin{bmatrix} x_r \\ y_r \end{bmatrix} = \begin{bmatrix} \cos\beta & \sin\beta \\ -\sin\beta & \cos\beta \end{bmatrix} \begin{bmatrix} x \\ y \end{bmatrix} \quad (34)$$

The line joining $(-d, 0, 0)$ and $(x_r, y_r, z)$ is given by:

$$x = -d + at \quad (35)$$
$$y = bt \quad (36)$$
$$z = ct \quad (37)$$

$$t_0 = \sqrt{(x_r + d)^2 + y_r^2 + z^2} \quad (38)$$

$$a = x_r + \frac{d}{t_0} \quad (39)$$

$$b = \frac{y_r}{t_0} \quad (40)$$

$$c = \frac{z}{t_0} \quad (41)$$

The intersection of this line with the detector plane occurs at:

$$x = 0 = -d + at \quad (42)$$

therefore:

$$t = \frac{d}{a} \quad (43)$$

$$y = bt \quad (44)$$
$$z = ct \quad (45)$$

The values (y,z) are used to determine the backprojected value by bilinear interpolation on the detector grid.

5. G2 phantom simulation

Figure 23:
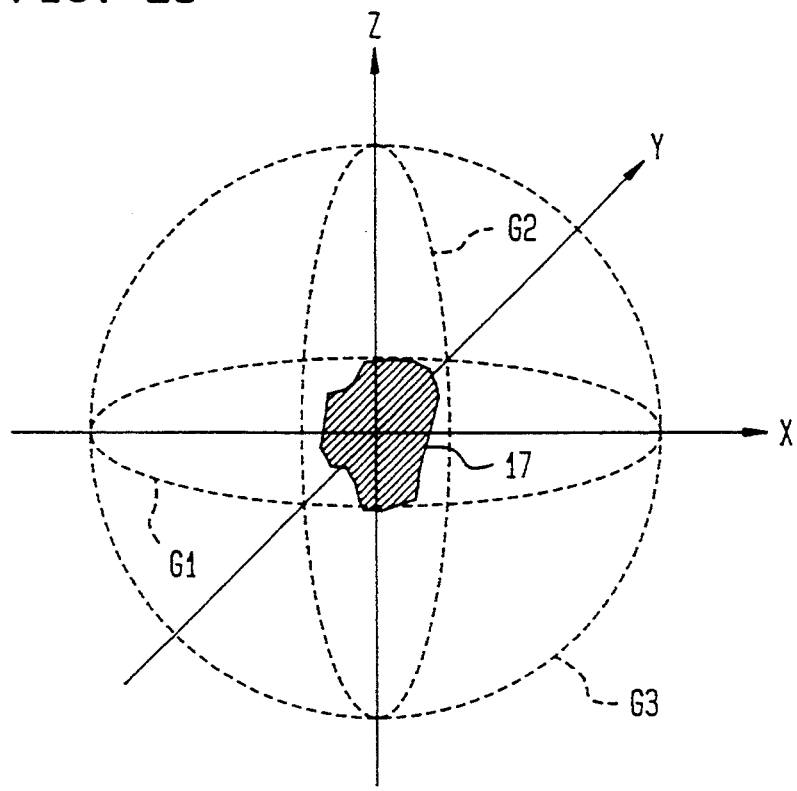
FIG. 23 is a more detailed pictorial diagram of FIG. 3 for illustrating the definition of three perpendicular great circles G1, G2, and G3 traced by the vertex of a cone beam.
Figure 24A:
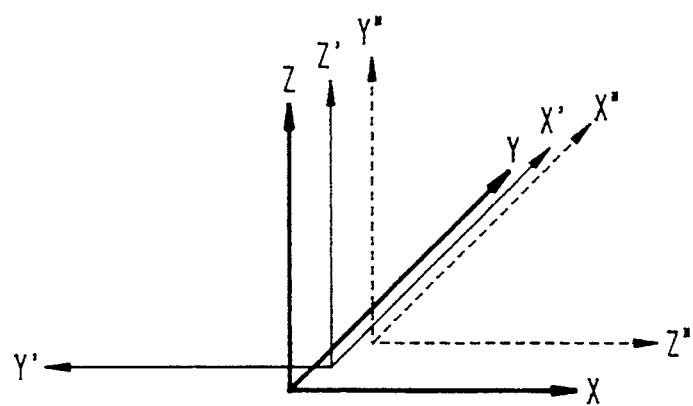
FIGS. 24A and 24B are diagrams for showing the coordinate transformations for a great circle G2, and a great circle G3, respectively.

For purposes of illustration with phantoms it is simpler to keep the source-detector assembly fixed on the x axis and vary instead the angle of the phantom to simulate rotation in the G2 and G3 planes. Having performed the scan with the source-detector assembly 1 in the x-y plane, one must next perform the same operation in the y-z plane (see FIG. 23). Keeping the object 17 fixed, one can rotate the coordinates by $\pi/2$ about the z axis to a coordinate system $(x',y',z')$ where $z=z'$. Next, rotate by $\pi/2$ about the x' axis to obtain the new coordinate system $(x'',y'',z'')$. It is clear from FIG. 24A that one now effectively has the scanning geometry as G1, only now the source 5 and detector 7 will move in the $(x'',y'')$ plane. The following steps must now be pursued:

Starting with an ellipsoid in (x,y,z) system (see FIGS. 23 and 24A):

$$\left(\frac{x-x_0}{A}\right)^2 + \left(\frac{y-y_0}{B}\right)^2 + \left(\frac{z-z_0}{C}\right)^2 = 1 \qquad (46)$$

with rotation of the coordinates by $\pi/2$ about z:

$$\begin{bmatrix} x' \\ y' \end{bmatrix} = \begin{bmatrix} 0 & 1 \\ -1 & 0 \end{bmatrix} \begin{bmatrix} x \\ y \end{bmatrix} \qquad (47)$$

$$x' = y \qquad (48)$$
$$y' = -x \qquad (49)$$
$$z' = z \qquad (50)$$

the ellipsoid in the (x',y',z') system is now:

$$\left(\frac{-y'-x_0}{A}\right)^2 + \left(\frac{x'-y_0}{B}\right)^2 + \left(\frac{z'-z_0}{C}\right)^2 = 1 \qquad (51)$$

Rotate by $\pi/2$ about the x' axis, using:

$$\begin{bmatrix} y'' \\ z'' \end{bmatrix} = \begin{bmatrix} 0 & -1 \\ 1 & 0 \end{bmatrix} \begin{bmatrix} y' \\ z' \end{bmatrix} \qquad (52)$$

$$y'' = z' \qquad (53)$$
$$z'' = -y' \qquad (54)$$
$$x'' = x' \qquad (55)$$

and the ellipsoid in (x'',y'',z'') system is:

$$\left(\frac{z''-x_0}{A}\right)^2 + \left(\frac{x''-y_0}{B}\right)^2 + \left(\frac{y''-z_0}{C}\right)^2 = 1 \qquad (56)$$

Lastly, one must rotate the ellipsoid by $-\beta$ to allow for rotation of the source. This is accomplished as follows:

$$\begin{bmatrix} x'' \\ y'' \end{bmatrix} = \begin{bmatrix} \cos\beta & -\sin\beta \\ \sin\beta & \cos\beta \end{bmatrix} \begin{bmatrix} x_2 \\ y_2 \end{bmatrix} \qquad (57)$$

Equation (56) is now:

$$\left(\frac{z_2-x_0}{A}\right)^2 + \left(\frac{x_2\cos\beta - y_2\sin\beta - y_0}{B}\right)^2 + \left(\frac{x_2\sin\beta - y_2\cos\beta - z_0}{C}\right)^2 = 1 \qquad (58)$$

One must repeat the procedure of finding the intersections of a line with the ellipsoid and the rest follows as before.

6. G3 phantom simulation

Figure 24B:
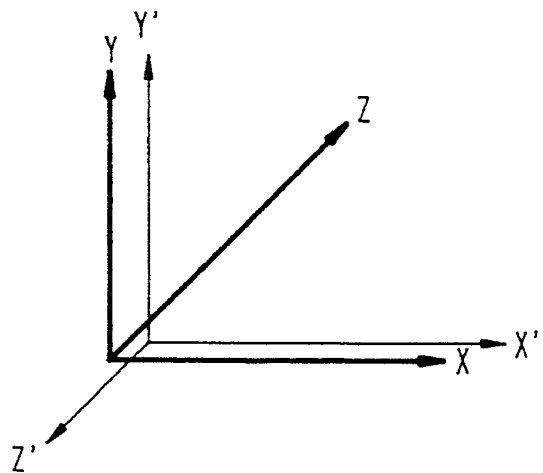

To perform a G3 scan, one must scan in the x-z plane. Therefore it is required to rotate the coordinates (x,y,z) by $\pi/2$ about the x axis (see FIGS. 23 and 24B). The equation for the ellipsoid in (x',y',z') is now:

$$\left(\frac{x'-x_0}{A}\right)^2 + \left(\frac{-z'-y_0}{B}\right)^2 + \left(\frac{y'-z_0}{C}\right)^2 = 1 \qquad (59)$$

Next, one must rotate the ellipsoid by $-\beta$ about the z' axis and the equation of the ellipsoid in the system where the source 5 and detector 7, in this example, are aligned along the x axis is:

$$\left(\frac{x\cos\beta - y\sin\beta - x_0}{A}\right)^2 + \left(\frac{-z-y_0}{B}\right)^2 + \left(\frac{x\sin\beta + y\cos\beta - z_0}{C}\right)^2 = 1 \qquad (60)$$

Figure 25:
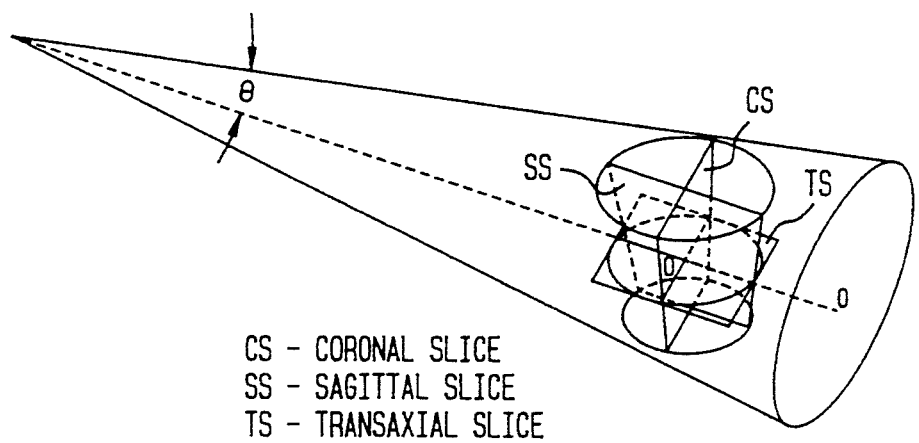
FIG. 25 is a diagram illustrating the definition of transaxial, coronal, and sagittal slices in an object relative to various embodiments in the invention.

The results of computer simulation tests for the present invention are described below. Note in FIG. 25, the conventional radiological definitions for orthogonal slices taken through a body. As shown by comparing FIG. 25 with FIG. 23, a transaxial slice TS is in the plane of a great circle G1; a coronal slice CS is in the plane of a great circle G2; and a sagittal slice is in the plane of great circle G3. The transaxial slice provides information relative to the horizontal spatial and contrast resolution, while the coronal slice displays the vertical resolution of the reconstruction. The x-y plane is defined as a horizontal plane. It is clear that for small values of z the reconstruction is similar to the fan beam reconstruction, therefore the horizontal resolution also can be expected to be similar. Use was made in the simulations of a phantom spherical skull with relative attenuation coefficient $\mu=2.0$ and uniform tissue inside with $\mu=1.02$. Onto this tissue inside test objects with $\mu$ varying from 0.01 to 0.003 have been selectively superposed. In this graph the attenuation relative to water is plotted as a function of z along a line in a coronal plane of a phantom object at x=y=0.1 centimeter. The thin disks of the phantom object are defined to be two voxels thick at the rotation axis, and appear over three mesh points.

However, when a coronal slice is simulated, the full extent of the missing data problem in the Feldkamp algorithm becomes evident. Test results were obtained to show a coronal plane at x=y=0.1 centimeter containing a resolution phantom consisting of a set of flat ellipsoids, which are 2 voxels thick in the z direction, placed at regular intervals along the z axis. The corresponding reconstruction using the Feldkamp algorithm was obtained (Curve G1 in FIGS. 26A, and 26B). The amount of degradation in both spatial and contrast resolution showed that the Feldkamp algorithm by itself can never be used for a realistic scanner. The artifacts arise because of what is termed "the missing data problem." Projection lines which are predominantly in the z direction are missing from data.

Figure 28A:
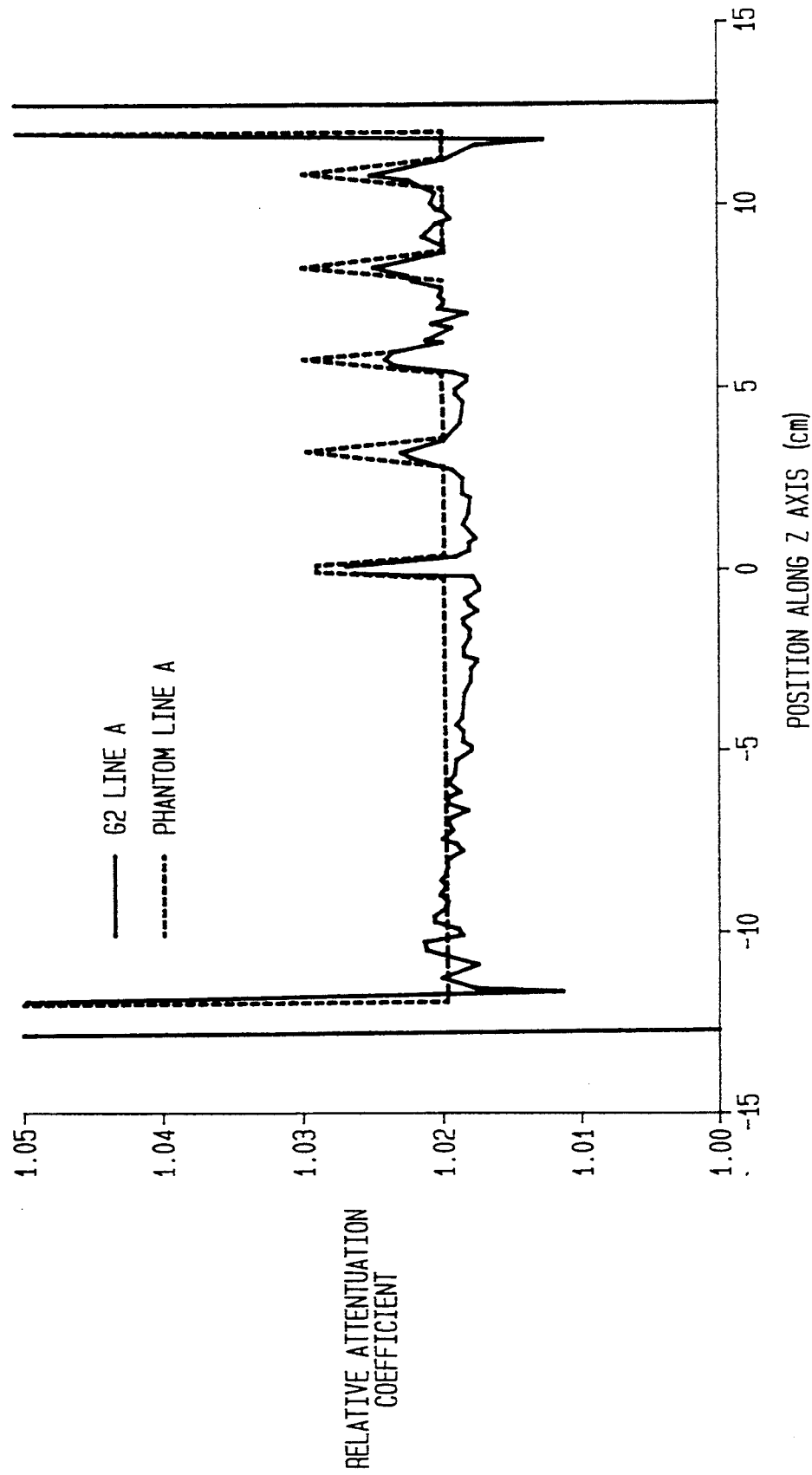
Figure 29:
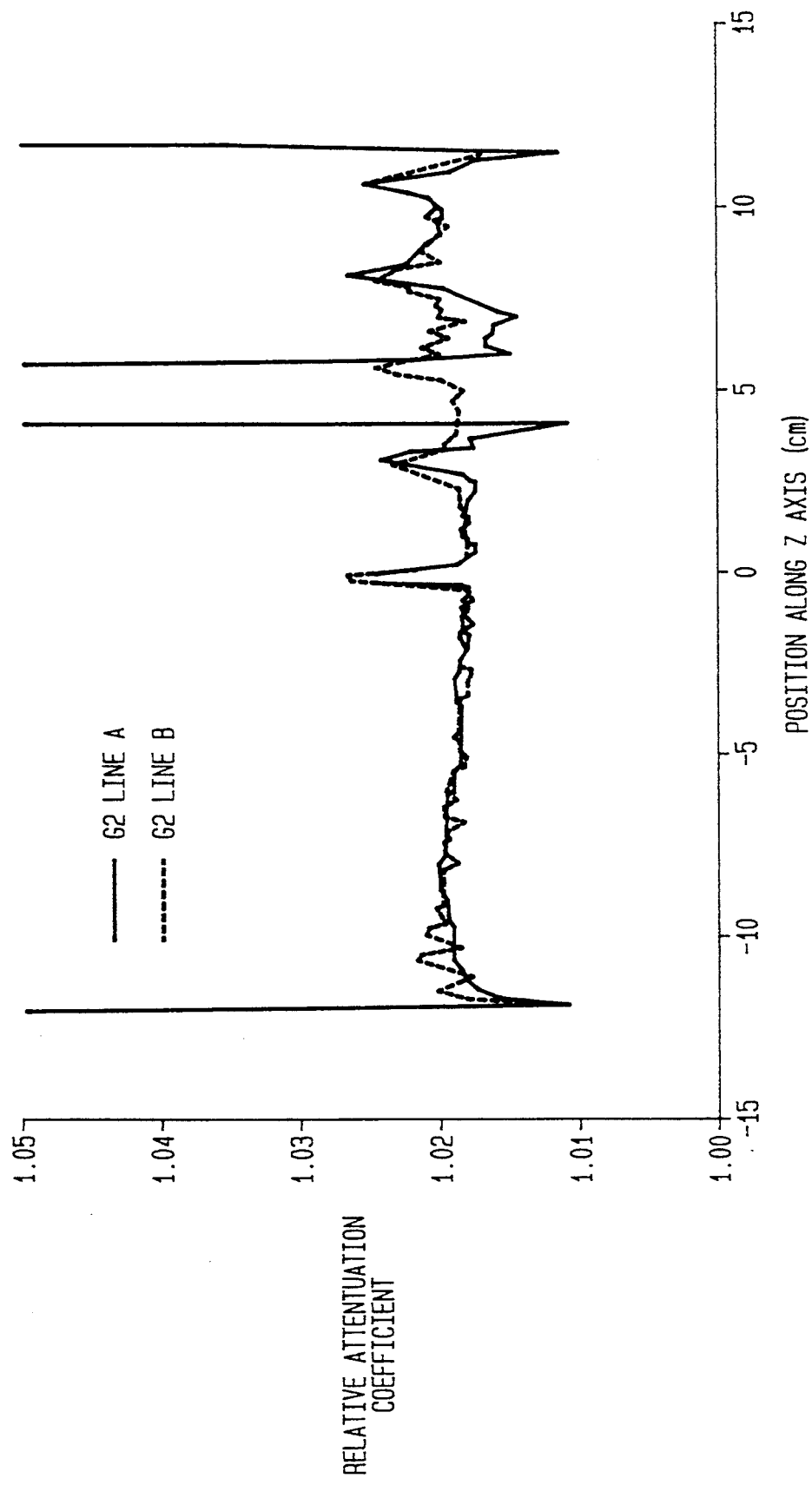
FIG. 29 is a graph showing simulated sections through a coronal plane.

For purposes of illustration, assume the source 5 is made to traverse two great circles (G1 and G2) of radius d about an object 17. This method is implemented here with a Feldkamp algorithm as the basic method of reconstruction after each scan. The advantage of the convolution backprojection method described above lies in that backprojecting need only continue onto the same mesh point when transferring to the next great circle. Programming wise, the subsequent scans are calculated using the same section of code as the first scan simply by performing a series of right handed coordinate transformations. Intuitively G2 is appealing because it fills in data in the second scan for G2 just where data is missing in the first scan for G1. FIGS. 28A, 28B and 29 show the improvement in resolution with a G2 scan (scanning in two orthogonal circular planes, i.e. G1 and G2).

Figure 26A:
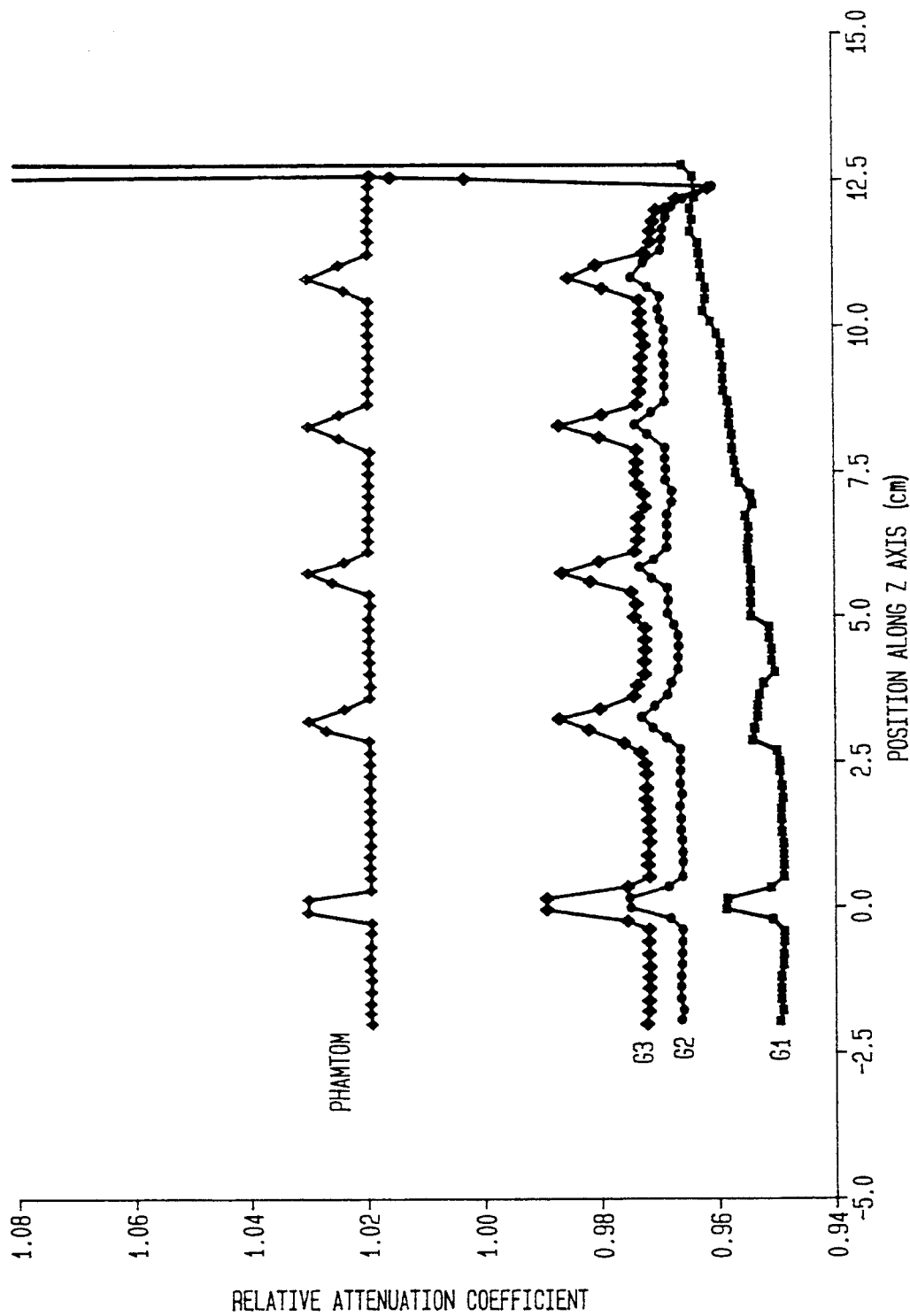
Figure 27:
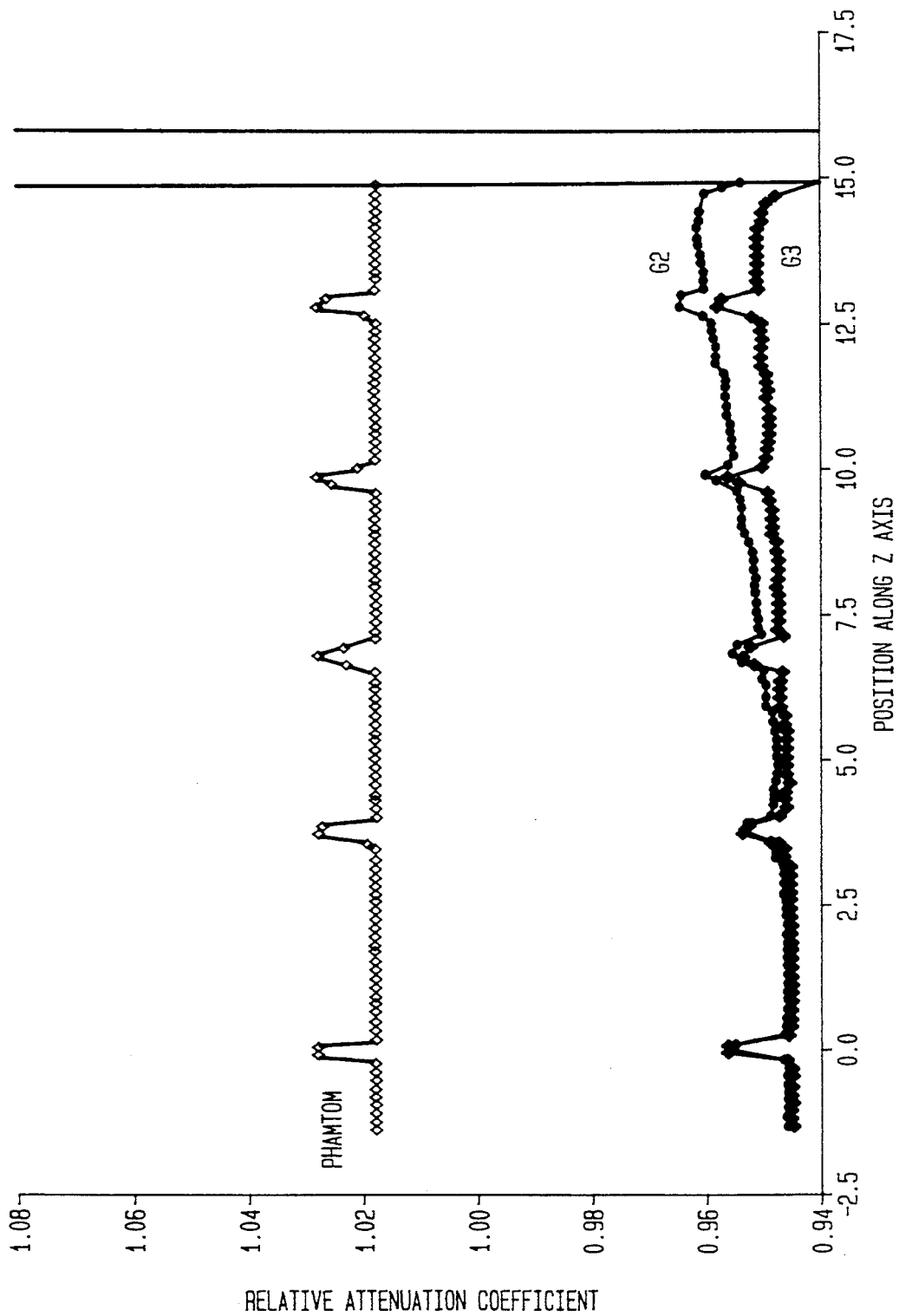
FIG. 27 is a graph showing for a large mesh, a line in a coronal plane at x=y=0.1 cm, with an attenuation of simulated thin disks of 10 HU (Hounsfield Units).

The present inventor's discovered that for completeness a third and final scan for G3 may be added perpendicular to the previous two scans for G1 and G2, as previously mentioned. The improvement with additional scans is substantial. This improvement is shown in the computer simulations of FIGS. 26A, 26B and 27. In these Figures, reconstructions are displayed more quantitatively. Curve 60 of FIG. 26B shows the "Phantom" to be reconstructed via simulated image scanning. Curves 62, 64, and 66, show the reconstructions of the phantom using a single scan (G1), a double scan (G1, G2), and a triple scan (G1, G2, and G3), respectively. The fact that the reconstruction peaks for 64 and 66 also do not extend over more than 3 mesh points indicate that the intrinsic spatial resolution of the algorithm must be $\leq 0.2$ voxel which is $\approx 0.04$ centimeter. As for contrast resolution, it was determined that a difference of 3 HU can be easily discerned. Note that there is little relative degradation in absolute value, spatial or contrast resolution as z increases. This is true particularly for reconstruction curve 66 (from G1, G2, G3 scans) giving the impression that almost any active volume can be achieved together with the ultra high resolutions. This effect can be seen clearly in FIG. 27 where the maximum z value is extended to about 15 cm.

Figure 30:
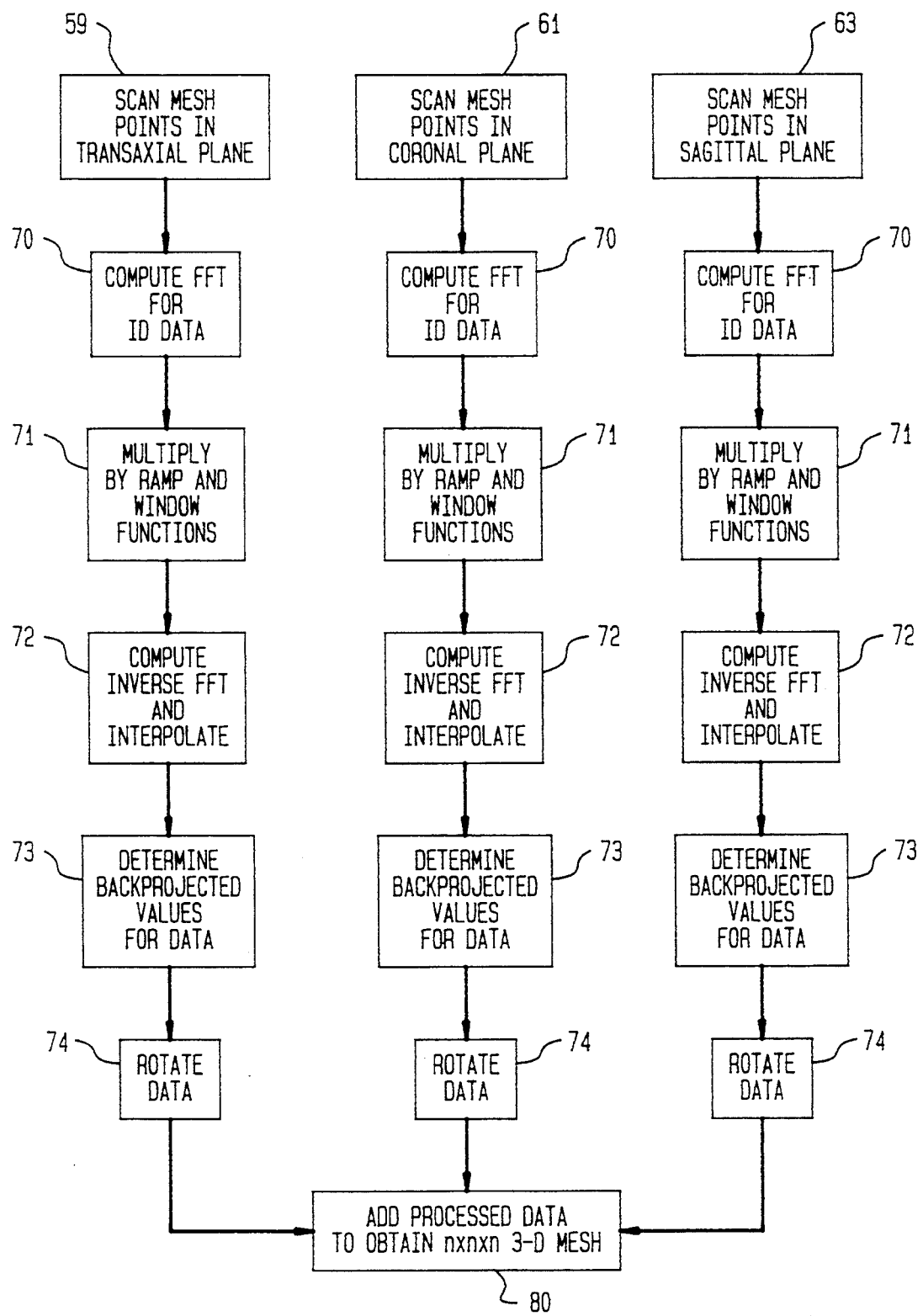
FIG. 30 shows a flowchart for processing data using an algorithm of one embodiment of the invention.

A flowchart is shown in FIG. 30 for illustrating in simplistic form the method of the invention described above. Typically, the terminology "slice" and "plane" are used interchangeably. As shown, the data from each one of transaxial slices TS, coronal slices CS, and sagittal slices SS about axes of revolution z, x and y, respectively, are processed individually by associated sequential steps 70 through 74. The processed data is then added together to provide an (M×M×M) 3-D mesh of reconstructed image points, which can be displayed on a standard video system, or printed out in a known manner.

More specifically, for a set of projection data to be processed line by line, as shown, the first step 70 is to perform a standard discrete Fourier transform (FFT) whose N components are defined as follows:

$$H_n = \sum_{k=0}^{N-1} h_k e^{2\pi i k n / N} \quad (61)$$

where n varies from 1 to N, and N must be equal to $2^m$ where m is a positive integer. The FFT output is then passed through a ramp filter and window multiplier 71, the mathematical processing being as shown in equations (16), (18), and (19), above.

The filtered data from step 71 is then processed in step 72 to take the inverse FFT, which is solved for $h_k$ as shown in equation (62) below:

$$h_k = \frac{1}{N} \sum_{n=0}^{N-1} H_h e^{-2\pi i k n / N} \quad (62)$$

Next, the inverse FFT data is used for the backprojection step 73, as shown in equations (34) through (45), to sum the contributions derived by interpolation from the associated detector plane 19 over all angles of the source 5 and detector 7 as it is rotated. Note that the interpolation provides for generating for each mesh point the point of intersection of a line between the source and the mesh point with the detector planes.

In step 80, the processed data at the mesh points from the three orthogonal planes are added together. The result is a 3-D mesh providing a reconstruction of the object for display, such as a 3-D display of a human body 9.

As shown above, in order to achieve better resolution in CT systems the single scan mode of operation must be replaced by the mechanically more complicated multiple scan mode of operation. However, this is not too high a price to pay since the resolution achieved with multiple scans is an order of magnitude better. This implies that CT scanners can now be designed whose performance will not be limited by the reconstruction algorithm at all.

With G2, the plane containing the source and detector assembly 1 will be at 45° on either side of the patient 9 who will remain stationary throughout the scan (see FIG. 2). Notice that the patient 9 has to lay sideways, that is perpendicular to the plane of the paper. This would minimize the illumination of the cone beam 21 through parts of the body 9 which are outside the active sphere, for these parts are not illuminated equally at all angles which may cause artifacts. The mount 11 of the source and detector assembly 1 has to be swiveled about the rotation axis by 90° after the first scan. As for a G3 scan, since the patient entry has to be in the middle of one of the octants carved up by the three perpendicular great circles G1, G2, G3, the radius of the sphere, that is the focal length of the system, has to be rather large. However, a G3 scan added to G1 and G2 scans provides the ultimate in resolution and active volume size unmatched probably by none other with the exception perhaps of complete spherical detection.

Although various embodiments of the present invention have been shown and described herein, they are not meant to be limiting. Those of skill in the art may recognize various modifications to these embodiments, which modifications are meant to be covered by the spirit and scope of the appended claims. For example, one may choose to reconstruct planes that are not close to the rotational or z axis. Also, the active volume being investigated or reconstructed can be extended by increasing the cone beam half angle $\theta$ as well as increasing the focal length. Also, the Feldkamp algorithm may be improved by replacing bilinear interpolation with non-linear interpolation. Also, one may derive a computer efficient 3-D algorithm providing greater accuracy than Feldkamp. Another is a source and detector assembly other than an x-ray based system, such as an ultrasonic system, an MRI type system, and so forth. Further note that in accordance with the invention, it is preferred that the angles between the planes be 90°, but angles less than or greater than 90° will also provide improved resolution in accordance with the methods and apparatus of the present invention.

Although preferred embodiments of the invention provide for the source and detector assembly to rotate about an object under investigation, an equivalent result in an alternative embodiment can be obtained with a stationary source/detector assembly and rotation of the object therebetween. Also, although the various embodiments of the invention are shown for use in scanning a human body, the invention is also applicable for use in scanning inanimate objects. In addition, the invention is useful in electron beam deflection CT systems, such as available from Imatron Corporation, in South San Francisco, Calif.

What is claimed is:

1. In a computer tomography system, including at least one assembly having an x-ray source and opposing x-ray detector, said system being operable for relative rotation between said assembly and an object within said assembly under study, a method for obtaining a 3-D (three-dimensional) data set from which 2-D (two-dimensional) or 3-D images can be obtained of a portion of said object comprising the steps of:

providing relative rotation between said assembly and said object in a first plane, for scanning to obtain related two-dimensional projection data;

providing relative rotation between said assembly and said object in a second plane substantially perpendicular to said first plane, for obtaining related projection data;

providing relative rotation between said assembly and said object in a third plane substantially orthogonal with said first and second planes, for obtaining related projection data; and processing said data from each one of said first through third substantially orthogonal planes for obtaining a 3-D mesh of data representative of a portion of said object.

2. The method of claim 1, wherein said rotating steps further include said first plane being a transaxial plane, said second plane being a coronal plane, and said third plane being a sagittal plane.

3. The method of claim 1, wherein said processing step includes the steps of:

individually computing the 1-D (one-dimensional) fast Fourier transform (FFT) for the projection data line by line, and for each source position within the rotational scan, respectively;

multiplying the FFT by a ramp function;

filtering the data in Fourier space from the said projections;

individually computing the inverse FFT's for the filtered FFT's of the data from the said filtered data;

generating for each mesh point the point of intersection of a line between the source and the mesh point with a plane of said detector via interpolation;

individually backprojecting the interpolated processed data for convolved data;

individually rotating the source and detector assembly to the next angular position;

repeating the prior six steps for scanning said first through third planes; and adding together the rotated data to obtain a 3-D mesh of said data representative of a portion of said object.

4. The method of claim 3, wherein said filtering steps each include the steps of:

multiplying said FFT's of the data from said first through third planes by a predetermined ramp function and a predetermined window function.

5. The method of claim 3, wherein said rotating steps further includes said first plane being a transaxial plane, said second plane being a coronal plane, and said third plane being a sagittal plane.

6. In a 3-D computer tomography system, the method comprising the steps of:

scanning mesh points in a plurality of substantially orthogonal planes associated with an object under investigation to obtain two-dimensional image data related thereto for each plane, respectively;

processing the image data obtained from each plane via sequential steps including:

computing the fast fourier transform (FFT);

multiplying by ramp and window functions for filtering the FFT;

computing the inverse FFT;

interpolating and backprojecting the inverse FFT;

rotating to the next scanning plane; and adding together the processed backprojected values from each plane for providing a 3-D mesh of said image data.

7. The method of claim 6, wherein said plurality of substantially orthogonal planes consist of transaxial, coronal, and sagittal planes, respectively.

8. The method of claim 6, wherein said plurality of substantially orthogonal planes include three great circles G1, G2, and G3, respectively, in which a source and detector assembly rotate around said object for providing said scanning steps.

9. A 3-D computer tomography system, comprising:

first through third two dimensional x-ray detectors;

first through third x-ray scanning assembly means each operable for rotating about an object in first through third substantially orthogonal planes, respectively, for obtaining image data on said first through third two dimensional x-ray detectors, respectively; and processing means for processing said data from each one of said first through third substantially orthogonal planes, for obtaining a 3-D mesh of data representative of a portion of said object.

10. The system of claim 9, wherein each one of said first through third two dimensional image detectors consists of an image intensifier.

11. The system of claim 9, wherein each one of said first through third two dimensional image detectors consist of a two dimensional array of individual detectors.

12. The system of claim 9, wherein said first through third planes consist of transaxial, coronal and sagittal planes.

13. The system of claim 9, wherein said processing means includes a computerized controller programmed to simultaneously process the data from each plane for computing the fast Fourier transform (FFT) thereof, filtering the FFT, computing the inverse FFT, backprojecting the inverse FFT, and rotating the backprojected data, whereafter the rotated data from each plane is added together to provide a 3-D mesh of data representing a portion of said object.

14. The system of claim 13, wherein said computerized controller is programmed to provide filtering of the FFT by multiplying the FFT by both a predetermined ramp and window function.

15. In a computer tomography system, including at least one assembly having an x-ray source and opposing x-ray detector, said system being operable for relative rotation between said assembly and an object under study, a method for obtaining a 3-D image of a portion of said object comprising the steps of:

providing relative rotation between a source and detector assembly about said object in a first plane, for rotationally scanning said object to obtain related two-dimensional projection data;

providing relative rotation between a source and detector assembly and said object in a second plane substantially perpendicular to aid first plane, for rotationally scanning said object to obtain related projection data;
individually computing the fast Fourier transform (FFT) for the projection data for each singular position within the rotational scan, respectively;
multiplying the FFT by a ramp function;
filtering the data in Fourier space from the said projections at each angular position;
individually computing the inverse FFT's for the filtered FFT's of the data from the said filtered data;
individually interpolating and backprojecting the Fourier processed data for convolved data;

individually rotating the source detector assembly to the next angular position;
repeating the prior six steps for scanning said second plane; and
adding together the rotated data to obtain a 3-D mesh of said data representative of a portion of said object.

16. The method of claim 15, wherein said filtering steps each include the steps of:
multiplying said FFT's of the data from said first and second planes by a predetermined ramp function, and a predetermined window function.

* * * * *